United States Patent [19]
Kaji

[11] Patent Number: 6,142,931
[45] Date of Patent: Nov. 7, 2000

[54] GUIDE TUBE UNIT FOR ENDOSCOPE AND METHOD FOR RESECTING A TISSUE

[75] Inventor: Kunihide Kaji, Fuchu, Japan

[73] Assignee: Olympus Optical Co., Ltd., Tokyo, Japan

[21] Appl. No.: 09/164,721

[22] Filed: Oct. 1, 1998

[30] Foreign Application Priority Data

Oct. 6, 1997 [JP] Japan .................................. 9-272716
Sep. 11, 1998 [JP] Japan ................................ 10-258373

[51] Int. Cl.$^7$ ............................... A61B 1/00; A61B 1/31
[52] U.S. Cl. ........................ 600/114; 600/102; 600/105
[58] Field of Search ................................ 600/102, 104, 600/105, 114, 125, 129, 130, 135, 136, 137; 606/1

[56] References Cited

U.S. PATENT DOCUMENTS

| | | |
|---|---|---|
| 4,538,594 | 9/1985 | Boebel et al. |
| 4,620,547 | 11/1986 | Boebel ................................... 600/567 |
| 4,807,593 | 2/1989 | Ito ............................................ 600/114 |
| 5,486,155 | 1/1996 | Muller et al. .......................... 600/137 |

FOREIGN PATENT DOCUMENTS

| | | |
|---|---|---|
| 83 16 987 U | 11/1983 | Germany . |
| 3319049 C2 | 5/1984 | Germany . |
| 91 15 741 U | 4/1992 | Germany . |

*Primary Examiner*—John P. Leubecker
*Attorney, Agent, or Firm*—Frishauf, Holtz, Goodman, Langer & Chick, P.C.

[57] ABSTRACT

An endoscope guide tube unit of the present invention comprises an outer sheath inserted into a body cavity of a human subject, an inner sheath arranged inside the outer sheath and a scope fixing tool provided on a proximal-end side. In the endoscope guide tube unit, an opening treatment window is provided as a side opening in a side wall area of the outer sheath near its distal end. The inner sheath is inserted to a position where the treatment window faces an affected region in the body cavity of a human being. It is possible to block the treatment window in the outer sheath. The affected region is treated via the treatment window opened in the outer sheath.

37 Claims, 14 Drawing Sheets

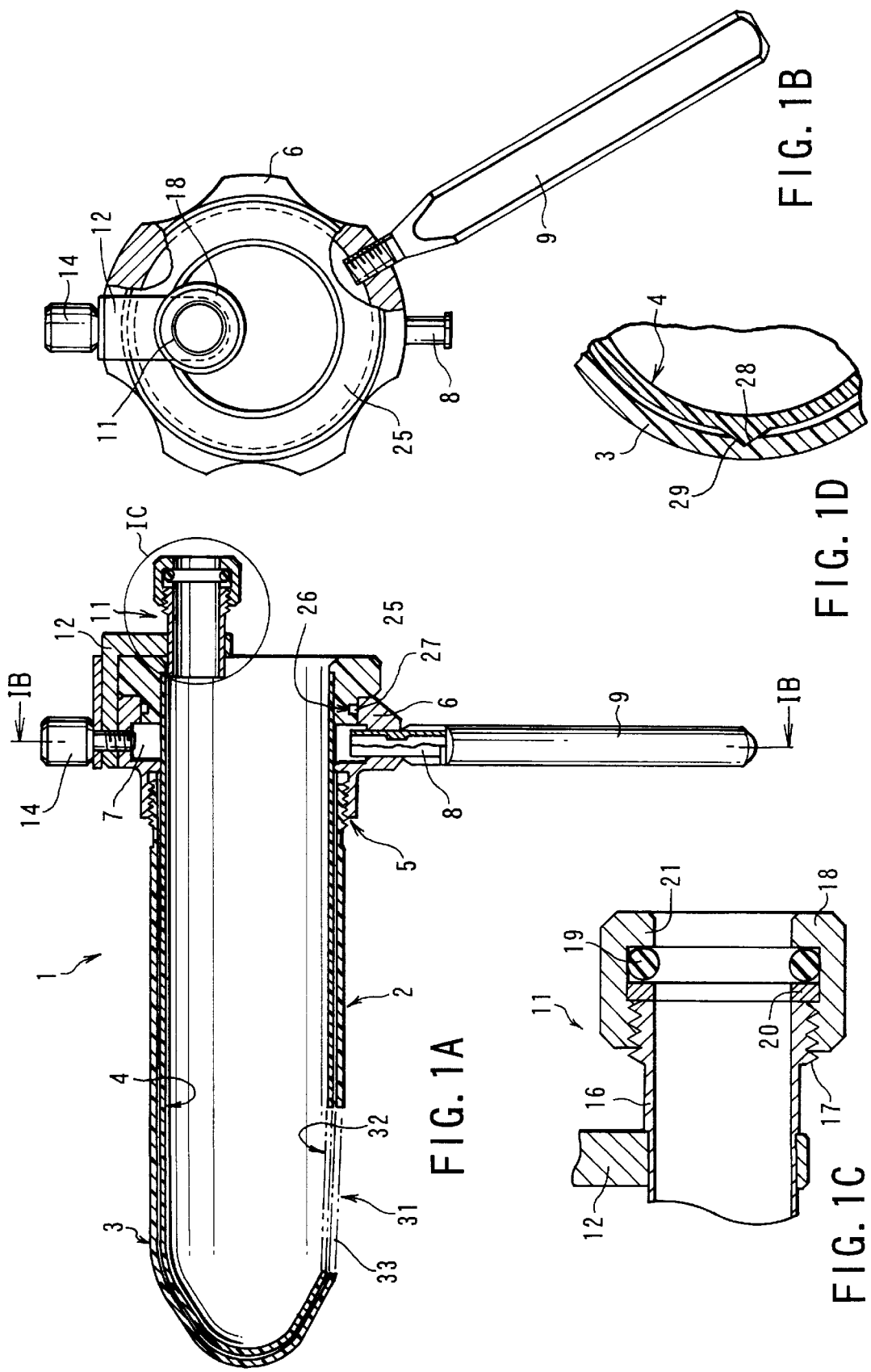

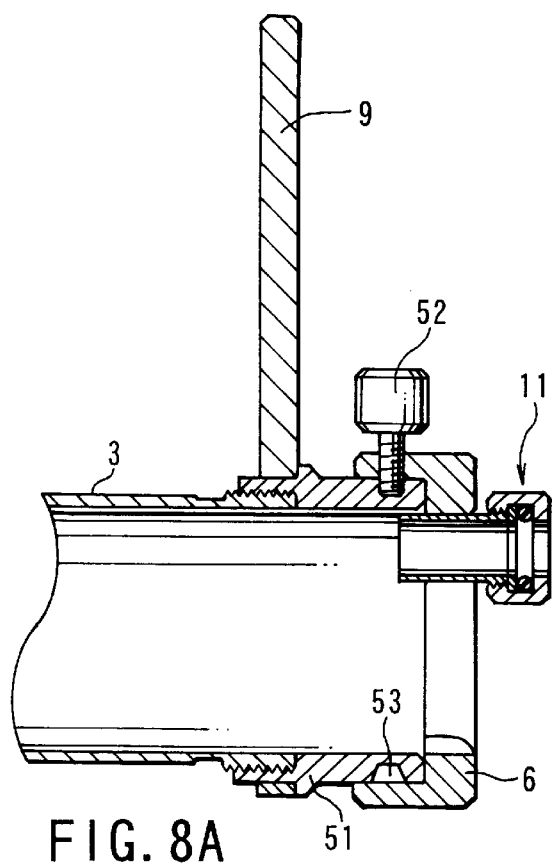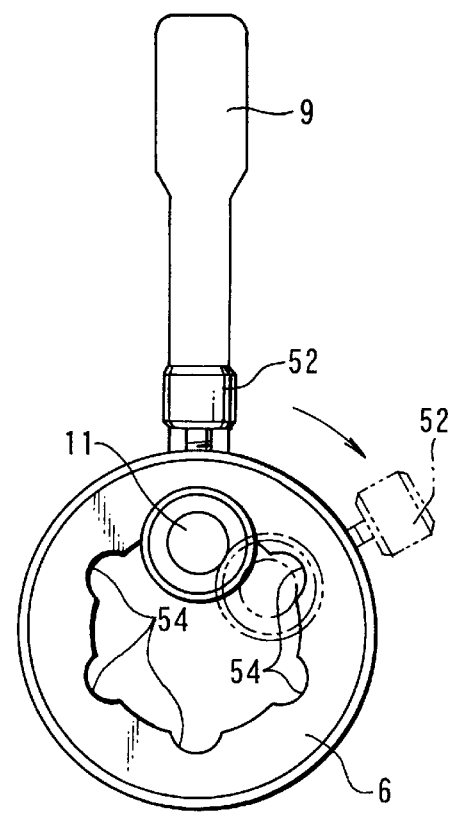
FIG. 8A
FIG. 8B
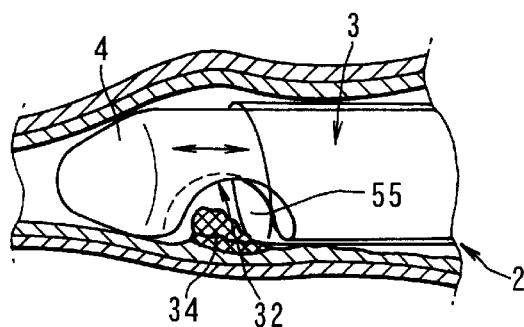
FIG. 9
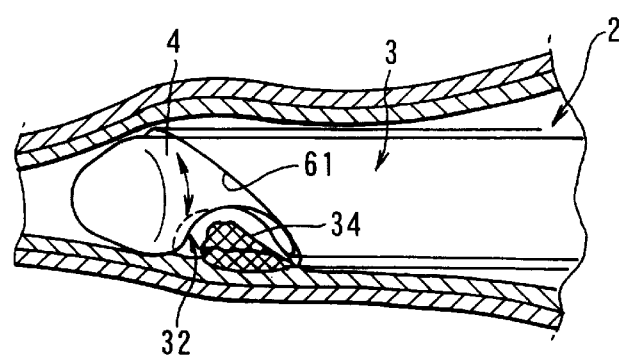
FIG. 10

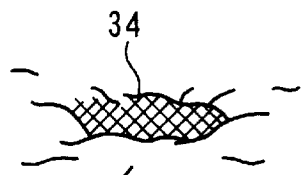
FIG. 20A
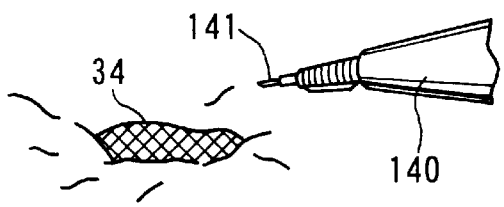
FIG. 20B
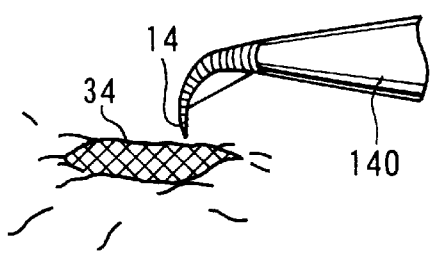
FIG. 20C
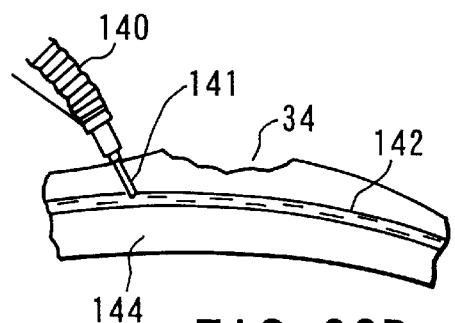
FIG. 20D
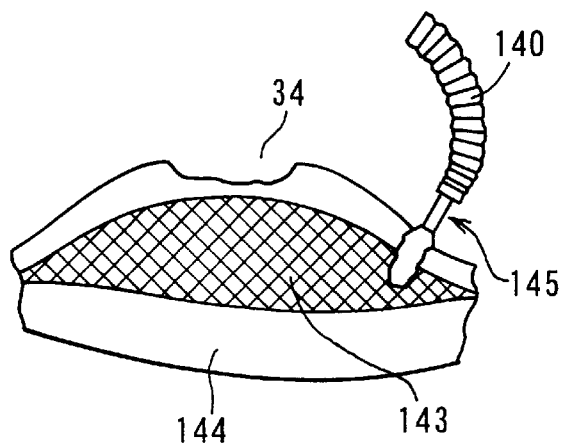
FID. 20E
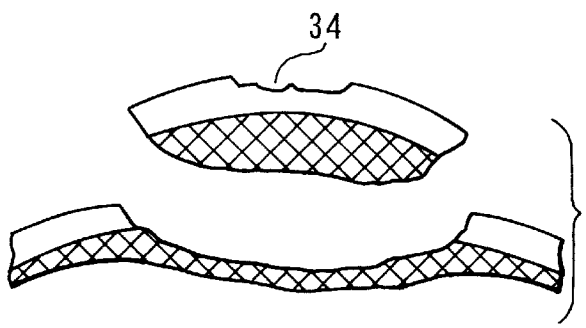
FIG. 20F

GUIDE TUBE UNIT FOR ENDOSCOPE AND METHOD FOR RESECTING A TISSUE

BACKGROUND OF THE INVENTION

The present invention relates to an endoscope guide tube unit and a tissue resecting method for use, for example, as a rectoscope for performing a treatment through the anus, and as a guide tube unit for guiding a laparoscope into a narrow site in a treatment tract upon surgical operation under the laparascope.

Conventionally, the surgical operation to be performed through the anus of a human subject is broadly classified into (1) a through-the-anus surgical operation through a direct observation under an anoscope and (2) a mucosa resecting procedure endoscopically performed under an optical system (hereinafter referred to as a scope) fitted in a cylindrical member initially inserted into the anus of the human subject and having a size somewhat greater than the anoscope.

The mucosa resecting procedure (2) using such an endoscope can be applied to a considerably deeply-seated lesion as compared with a directly observed surgery (1) under the anoscope. The sheath of the guide used for the procedure (2) is 40 mm in outer diameter and about 10 to 20 cm in length. The forward end portion of the sheath is diagonally cut away and the proximal-end portion of the sheath is hermetically sealed with an air-tight connector. In use, the endoscope is hermetically fixed in place at the connector and a treating tool, such as forceps, is hermetically inserted into an inside and the procedure is carried out while making an observation under the endoscope. At that time, a $CO_2$ gas is sent via the sheath into the rectus where a treatment space is positively created due to the expansion of the rectus with the $CO_2$ gas.

Further, upon the resection of the mucosa, a physiological salt solution is injected below the mucosa to cause that area to be raised. By doing so, the mucosa is cut off with a high-frequency current. After the cutting off of the mucosa, the parts of the cut area are stitched together, thus ensuring an earlier recovery and preventing a narrowing from occurring due to ulceration at that cut region. It is required that a suture line be formed in a direction perpendicular to the longitudinal axis of the intestinal tract.

According to these methods, it is possible to cut off the lesion in the body of the patient without the need to open his or her body wall and it is useful from an invasive standpoint.

In the case where the procedure (2) is not used, the abdomen is dissected as a replacement procedure and a very great invasive procedure is required, such as a "forward removal" by cutting the rectus and a trans-sacral removal by cutting the side portion of a tailbone and sub-sacral bone down to the neighborhood of the anus. It is said that the procedure of the removal of the mucosa, under the endoscope, through the anus is very useful to the patient.

As the surgical instrument, there is a connector-equipped sheath, for example, in U.S. Pat. No. 4,538,594 and DE 3319049 C2. This can be used for procedure by the insertion and holding in place of an optical device (scope) and forceps.

Further, a double-sheath unit is known in GM 91 15 741.2, having a similar structure to that shown above and, in particular, an inner and an outer tube projecting from the outer tube and exchangeable with a new one.

Still further, a rectoscope having a similar structure is also known in GM 83 16 987.3 in which an opening is provided in the side wall of a distal-end portion of a sheath to be inserted into the rectus through an anus and a connector with a light source cable mounted thereon is rotatably mounted on a proximal-end side of the sheath and, upon the insertion and withdrawal of the sheath, the opening of the sheath is closed by a closing means.

In the case where any treatment is performed on a narrow cavity by a surgical operation under a laparoscope, it has been the usual practice to, while creating a treating space with the use of a plurality of forceps and excluding tool, treat that region of interest by another forceps, etc.

In U.S. Pat. No. 4,538,594, DE 3319049 C2 or GM 83 16 987.3, a treatment is performed by injecting a $CO_2$ gas into the rectus through a sheath and expanding the rectus with the $CO_2$ gas. A port with a hermetic seal maintaining means is provided on a connector section so as to insert forceps, etc., into a region when a gas is sent there. Therefore, the forceps, etc., for treatment is gripped at the hermetic seal section and, upon the operation of the forceps, etc., that operation or operations are considerably restricted at that hermetic seal section-equipped port side acting as a fulcrum. In order to cover such a restricted movement, the forward end portion of the forceps, etc., is so designed as to be somewhat bendable. If, that end portion is so bent, then the operability of the forceps, etc., is affected, so that a treatment has to be performed under a very difficult condition.

Further, as shown in FIG. 21A, a treatment space 200 at a rectus expanded with a gas provides a three-dimensional space deeper from an obliquely opened end position of a sheath 201. For this reason, the treating operation in the treatment space 200 has to be done under a complicated three-dimensional motion and a higher degree of skill, coupled with the operational difficulty, has been needed under these situations.

After the insertion of the sheath into the rectus, it is so positionally set as if to look down onto a lesion 202 from an obliquely opened end of its distal end side through the treatment space 20. Further the treatment space 200 is three-dimensional and, in addition, the lesion 202 also takes various positions though depending upon the running of the rectal tract, so that the treatment has often been performed under a difficult condition. In the case where any lesion 202 is situated at an upper, a middle or a lower rectal valve and, in particular, at the backside of a valve so-called the rectal folds 203, the treatment space becomes difficult to observe under a scope 204 due to it defining the deeper three-dimensional space as set out above. Moreover, the lesion 202 also becomes difficult to obtain in a visual field. Thus it has been fairly difficult in actual practice to appropriately perform a treatment including the removal of the mucosa.

Further, when, after the removal of the lesion 202, the parts of the cutting region are stitched together, that suture line has to be oriented toward the direction perpendicular to the longitudinal axis of the intestine. If this direction is wrongly taken, then there is a possibility that a narrowing is created in the intestinal tract. Thus a careful operation is needed upon suture. Further, the sheath 201 is maintained in a hermetic state and the stitching method is a continuous suture done by a general surgery under a laparoscope, thus involving a difficult operation of, for example, correctly passing a thread needle from the forceps on one side to the forceps on the other in the sheath 201.

Since, in the above technique, generally, the longer the sheath, the smaller the degree of freedom with which the forceps are oriented, that is, in particular, the smaller the angle at which the suture line is oriented relative to the longitudinal direction of the intestinal tract, it follows that, under these situations, the deeper the lesion is situated, more difficult an operation is needed.

Further, various types of special-purpose tools/instruments are required, such as a gas supply device, a smoke removing device upon conduction with a high frequency, a sealing member at a connector, etc.

In order to avoid these situations, another method has also been attempted whereby no air is conducted (no connector is provided). FIG. 21B shows the method according to which an oblique distal-end portion of a sheath 201 is pushed against a lesion 202 without passing any gas thereto and, by doing so, a treatment is performed there at that operation field. Generally, a mucosal tissue 206 of the rectal tract is more distensible and, if the distal-end portion 205 of the sheath 201 is pushed against the mucosal tissue 206, the mucosal tissue portion enters clear of a sheath's distal-end 205 into this sheath 201, so that the lesion 202 is much less extended/distended. It is actually difficult to, in this state, cut off that layer region of the mucosal tissue 206. And there is a risk that the region will be pierced instead of being cut off or partly left as it is. This forces the operator to take a very careful operation under a difficult condition.

The design of not supplying any gas eliminates the need to provide a corresponding special-purpose device, indeed, and adds the degree of freedom because the associated forceps as a whole can be moved without the need to provide any fulcrum there. This advantage is offset by the disadvantage that, since, conversely, the mucosal tissue portion of the intestinal track glides into the opening of the distal end portion of the sheath, the lesion cannot be adequately developed and be difficult to obtain along a planned cutting-off line.

Since, upon surgery under the laparascope, a treatment is performed at a narrower tract, this procedure is very cumbersome and there is a poor development of the region in a surgery field, so that, if there occurs the bleeding, etc., it is difficult to control.

As set out above, the conventional procedure has a merit in one aspect but a demerit in another aspect and is difficult, thus requiring a skilled technique.

BRIEF SUMMARY OF THE INVENTION

It is accordingly an object of the present invention to provide an endoscope guide tube unit which, while being relatively simpler in construction, allows a treating region to be distended under a better condition, ensures a greater degree of freedom with which a treatment tool is operated, and can safely and readily perform a treatment, such as the cutting off/sewing, on a target region and to a method for cutting off a target tissue with the use of the endoscope guide tube unit.

In order to solve the above-mentioned task, there is provided an endoscope guide tube unit for allowing an endoscope to be inserted therein and a treatment tool to be inserted therein so that, while observing an affected region under the endoscope, the affected region is treated, comprising:

a first elongated sheath-like member adapted to be inserted into a body cavity of a subject and having a side wall section and a closed distal-end section and having a mouth section at a proximal end to allow the endoscope and treatment tool to be inserted therein, the side wall section having an opening through which the affected region is treated;

a holder provided on a proximal-end side of the first sheath member to hold the endoscope in place; and a second sheath-like member telescopically inserted into the first sheath-like member and having a section for closing the opening.

According to the present invention, the second sheath-like member has a second opening provided by a side hole in the distal-end portion thereof and a treatment window is provided by a common area defined between the second opening and the opening of the first sheath-like member and is closed by displacing these openings away from each other.

In a second aspect of the present invention, there is provided an endoscope guide tube unit for allowing an endoscope to be inserted therein and a treatment tool to be inserted therein so that, while observing an affected region under the endoscope, the affected region is treated, comprising:

a first elongated sheath-like member adapted to be inserted into a body cavity of a subject and having a side wall section and a distal-end section and having a mouth section at a proximal-end side of the first sheath-like member to allow the treatment tool to be inserted therein, the side wall section having a first opening through which the affected region is treated;

a holder provided on a proximal-end side of the first sheath-like member and adapted to hold the endoscope in place which, in use, is inserted via the mouth section into the inside of the first sheath-like member; and a second sheath-like member telescopically inserted into the first sheath-like member and having a closing portion for closing the first opening and a second opening overlapped with the first opening, wherein the first and second sheath-like members are selectively relatively moved to a first position in which the first opening is closed with the closing portion of the second sheath-like member and to a second position in which the first and second openings are overlapped to provide a common opening area for defining a treatment window via which the affected region is treated.

In use, the first sheath-like member is inserted up to a position in which the opening of the first sheath-like member faces a lesion. By doing so it is possible to provide a treatment plane (mucosa plane) defined by the outer surface of the first sheath-like member. In the case where the second sheath-like member is used, for example, upon insertion into the rectal tract, this is done by closing the opening of the first sheath-like member with the second sheath-like member. By doing so it is possible to prevent any injury to the rectal tissue resulting from the presence of such opening. The endoscope, being held by the holding means, is better in operability.

It is also to be noted that a greater opening can be used at a distal-end connector in which case it is possible to increase the degree with which the treatment tool, such as the forceps, is operated. Further, if such a greater opening structure is used at the proximal-end side, a "direct-operation" sensation can be given to the user in comparison with an air-carrying type (hermetically sealing type), so that a treating operation is easier. Further, the discharge of a smoke at a time of high-frequency conduction is better effected. And upon sewing operation it is not necessary, unlike the air (gas) carrying type, to perform a difficult operation such as the passing of a needle by the forceps. It is also easier to draw the sewing needle to an outside in a stitch-by-stitch fashion and re-hold it in proper position. Since, upon suture, a mucosa-removing site is retained by the sheath-like members in a duct-like configuration, it is possible to avoid the situation in which the duct-like space is narrowed by the suture.

According to the present invention, upon insertion into the rectus for example, the guide tube unit is inserted up to the position where the lesion is brought to the opening of the first sheath-like member. By doing so it is possible to create a treatment plane (mucosa plane) defined by the outer surface of the first sheath-like member and thus perform a treatment normally in a stable state. Since the opening can be closed by the second sheath-like member, it is possible to prevent any injury to a tissue site. Further, a greater-opening structure can be provided at the proximal-end side and, in this case, a greater degree of freedom can be provided with which the treatment tool, such as the forceps, is operated. And a direct-operation feeling is given to the user. Still further, it is not necessary to perform a difficult operation such as the passing of the needle by the forceps, upon suture, as in the air (gas) carrying type. And the needle can be re-held in proper position. During these operations, the mucosa-removing site is kept, by the sheath-like member, in a duct-like configuration and it is easier to sew together parts of the mucosa-removing region. Further, there occurs no narrowing, upon suture, at that region. Thus the sewing together of the region can be readily accomplished. And it is also possible to better discharge a smoke at a time of high-frequency conduction. From the standpoint of necessary instruments and materials, less of these are simply required and a low-cost benefit can be obtained.

According to another aspect of the present invention, there is provided a method for cutting off a mucosa tissue in a deeper rectal tract with an endoscope guide tube unit, comprising the steps of:

inserting a thread-attached needle carrier into the endoscope guide tube unit via an associated connector and anchoring threads to the mucosa tissue through an opening created near a distal-end portion of the guide tube unit;

pulling the anchored threads from the connector to an outside past the interior of the endoscope guide tube unit;

drawing the guide tube unit off the rectal tract to leave the anchored threads only;

again inserting the guide tube unit into the rectal tract, while pulling the anchored threads along an outer surface of the guide tube unit;

drawing the threads further backward to a position where a target mucosa tissue portion can be treated via the opening;

fixing the threads to thread fixing means; and cutting off the mucosa tissue portion.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments give below, serve to explain the principles of the invention.

FIG. 1A is a view in longitudinal cross-section showing an endoscope guide tube unit according to a first embodiment of the present invention;

FIG. 1B is a back view, partly cut off, taken along line 1B—1B in FIG. 1A, showing the endoscope guide tube unit;

FIG. 1C is a view in longitudinal cross-section showing a scope fixing tool of the endoscope guide tube unit;

FIG. 1D is a cross-sectional view showing portions of a fitting area of outer and inner sheaths of the endoscope guide tube unit;

FIG. 8A is a view in longitudinal cross-section showing a proximal-end side area of an outer sheath of a second embodiment of the present invention;

FIG. 8B is a front view showing the proximal-end side area of the endoscope guide tube unit in FIG. 8A;

FIG. 9 is an explanative view showing an in-use state of an endoscope guide tube unit according to a third embodiment of the present invention;

FIG. 10 is an explanative view showing an in-use state of an endoscope guide tube unit according to a fourth embodiment of the present invention;

FIGS. 20A, 20B, 20C, 20D, 20E and 20F are explanative views showing the order of cutting off a mucosa tissue with the use of the endoscope guide tube unit of the sixth embodiment.

DETAILED DESCRIPTION OF THE INVENTION

First Embodiment

Figure 2A:
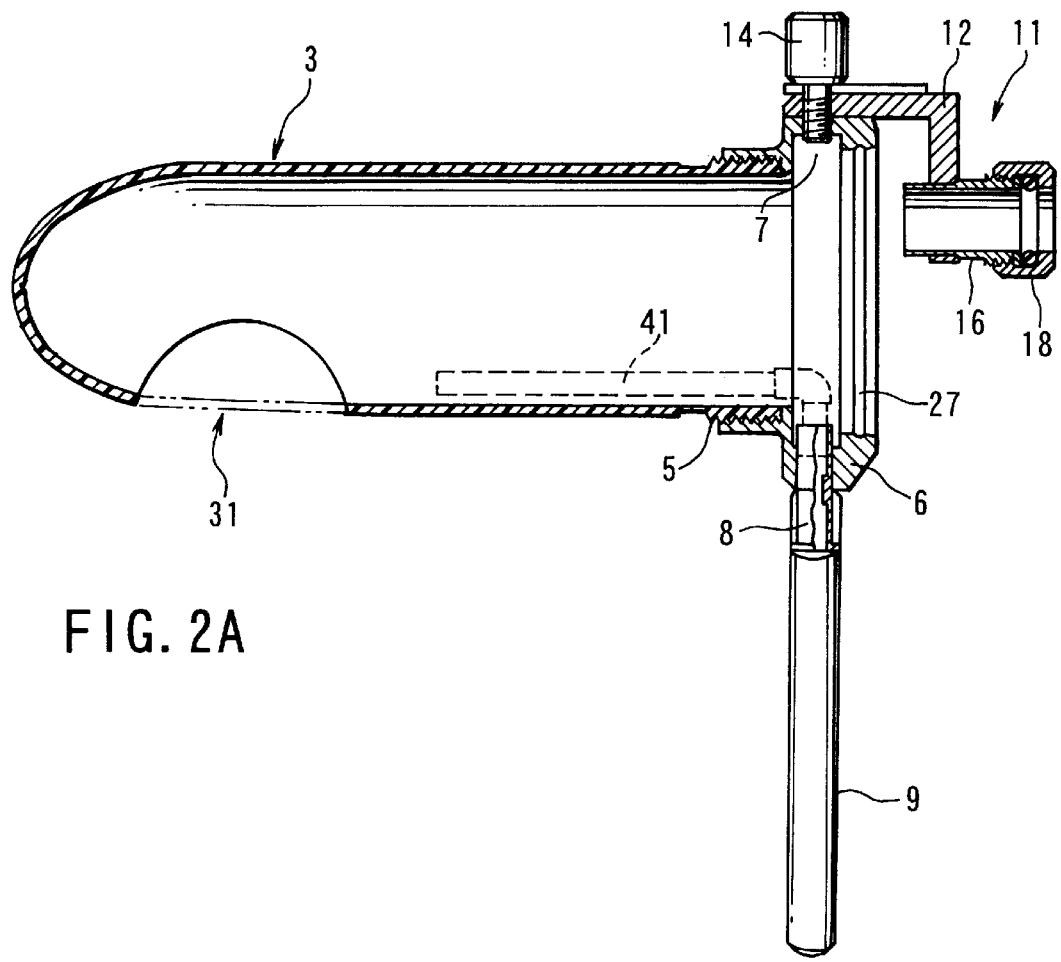
FIG. 2A is a view in longitudinal cross-section showing a sub-assembly of an outer sheath of the endoscope guide tube unit of the first embodiment.

An embodiment of the present invention will be explained below with reference to the accompanying drawing.

FIG. 1A is an explanatory view showing an arrangement of a body of an endoscope's guide unit 1, in an assembled state, according to a first embodiment of the present invention. The guide unit 1 has an insertion section 2. The insertion section 2 is of a double sheath type such that it comprises an outer sheath 3 serving as a first tube member and an inner sheath 4 serving as a second tube member and the inner sheath 4 is nestably fitted into the outer sheath 3. The outer sheath 3 and inner sheath 4 are each formed of a long, slender, thin-walled cylindrical tube. The distal-end portion of the respective sheath (3, 4) has a curved surface of a streamlined configuration at a distal-end section to allow it to be readily inserted into the rectal tract. The respective sheaths 3 and 4 are similar in configuration to each other and are mutually contacted with each other. The sheathes 3 and 4 are made of a transparent material, such as a resin, to allow an observation of a tissue situated in a position opposed to the distal-end section of the sheaths upon insertion. Further, in order to prevent any damage to be caused on a living tissue at a time of inserting the sheaths, the distal end portion of the sheaths 3, 4 may be so flexibly formed as to have a pliable recovery of an extent not to lose any insertion force.

Figure 2B:
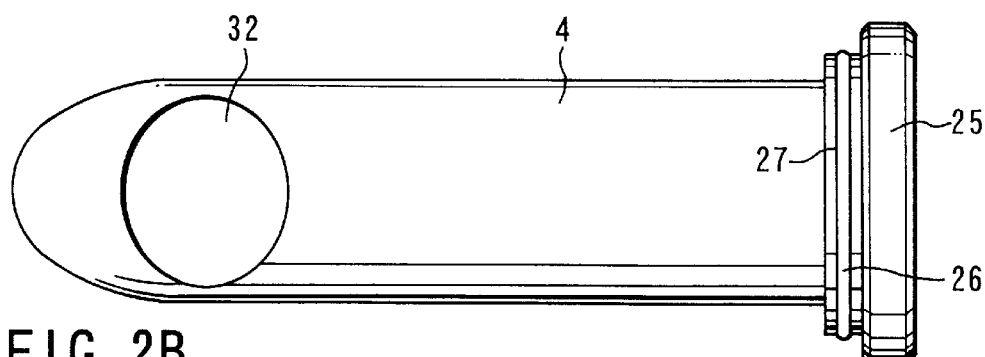
FIG. 2B is an explanatory view showing a sub-assembly of the inner sheath of the endoscope guide tube unit.

FIG. 2A shows a sub-assembly of the outer sheath 3 side and FIG. 2B a sub-assembly of the inner sheath 4 side.

A threaded area 5 is formed on outer periphery of a proximal-end portion of the outer sheath 3. The threaded area 5 is threadably connected to a ring-like first connector 6. The first connector 6 constitutes a connection structure detachably connectable to the outer sheath 3. For this reason, depending upon the depth of any lesion, the outer sheath 3 can be replaced by another outer sheath different in length from the outer sheath. The proximal-side end portion of the first connector 6 surrounds the outer circumference of the proximal-side end portion of the inner sheath 4, except the threaded portion relative to the outer sheath, and directly fitted on the outer circumference of the proximal-side end portion of the inner sheath.

In an intermediate portion of an inner wall of the first connector 6 a groove is provided around the full circle of the connector to provide a chamber 7 of a given volume at the inside of the first connector 6, as shown in FIG. 1A, when the outer sheet 3 and inner sheath 4 are set in an assembled state. The chamber 7 communicates with a Luer-lock type connector 8 and a clearance formed between the inner sheath 4 and the outer sheath 3. The chamber 7 is subjected to a suction force by an external suction tube, for example, connected to the Luer-lock type connector 8 as will be later described. By doing so, a suction is achieved through a clearance created between the inner sheath 4 and the outer sheath 3. Further, it is possible to achieve such suction through the first connector 6, chamber 7 and clearance between the inner sheath 4 and the outer sheath 3 or to supply a gas there as required. That is, the suction means and gas supplying means are incorporated at the endoscope's guide tube unit 1.

The Luer-lock type connector 8 communicating with the chamber 7 and a grip arm (grip section) 9 for supporting a whole structure of the endoscope's guide unit are fixedly mounted on the first connector 6. One end portion of an L-shaped arm 12 for supporting a scope fixing tool (holder) 11 of an endoscope holding means as will be set out below is detachably fixed by a fastening screw means 14 to the outer wall of the first connector 6.

When the arm 12 is attached to the first connector 6, the other end of the arm 12 is abutted against the proximal end surface portion of a later-described second connector 25 of the inner sheath 4 to prevent the second connector 25 from slipping out of the rest of the resultant structure. The arm 12 serves also as a stopper having a slipping-out preventing function relative to the inner sheath 24 (see the assembled state in FIG. 1A).

As shown in FIG. 1C, a cylindrical scope guide 16 of the scope fixing tool 11 is fixedly attached to said other end of the arm 12. The center axis of the scope guide 16 is substantially parallel to the center axis of the insertion section and the forward end portion of the scope guide 16 slightly extends toward the inner side of the insertion section 2 and confronts the inside of the insertion section 2 and opened there. A threaded portion 17 is formed on the outer periphery of the proximal-end portion of the scope guide 16 as shown in FIG. 1C. A fixing ring 18 is threadably fitted over the threaded portion 17. An elastic O-ring 19 and back-up ring 20 are internally fitted relative to the fixing ring 18. By inserting the scope (endoscope) 37 along the scope guide 16 and tightly threading the fixing ring 18 as set out above, the elastic O-ring 19 is pushed toward the axial direction of the fixing ring in a way to be situated between the back-up ring 20 and the fixing ring 18. At this time, the O-ring 19 is deformed and is bulged inwardly, whereby the outer periphery of the scope 37 is held in place and gripped. At that position, the scope 37 is fixed in place. The back-up ring 20 is made of a sliding material, such as Teflon. This prevents the O-ring 19 from being twisted and cut at a time of fixing the scope.

The second connector 25 is connected to the proximal-side end of the inner sheath 4 and has an opening substantially the same as the inner diameter of the outer sheath 3. The second connector 25 has an outer periphery of its forward end portion fitted on the inner periphery of the first connector 6. A fixing O-ring 26 is fitted on the outer peripheral surface of the forward end portion of the second connector 25. The O-ring 26 is fitted in an engaging groove 27 in the outer peripheral surface of the second connector 25. The first and second connectors 6 and 25 are hermetically connected to each other by the O-ring 26 and, in that hermetically held state, the inner sheath 4 and second connector 25 can be rotated in the outer sheath 3. In the case where the inner sheath 4 is detached from the outer sheath, the fixing screw 14 is detached from the first connector 6 and the scope fixing tool 11 together with the arm 12 is detached as one unit. By doing so, the inner sheath 4 can be withdrawn out of the outer sheath 3 and both can be disassembled from each other.

As shown in FIG. 1D, both the outer sheath 3 and inner sheath 4 constituting the insertion section 2 of the endoscope guide tube unit 1 are fitted together with a slight clearance left therebetween. At least one projection 28 is provided at the distal end of the inner sheath 4 and at least one recess 29 is provided in the inner surface of the outer sheath 3. By fitting the projection 28 into a selected recess 29 the inner sheath 4 and outer sheath 3 are connected together and, at a time of the rotation operation of the insertion section 2, the inner sheath 4 and outer sheath 3 are so fixed as not to be displaced in their axes and fitting positions.

Figure 3A:
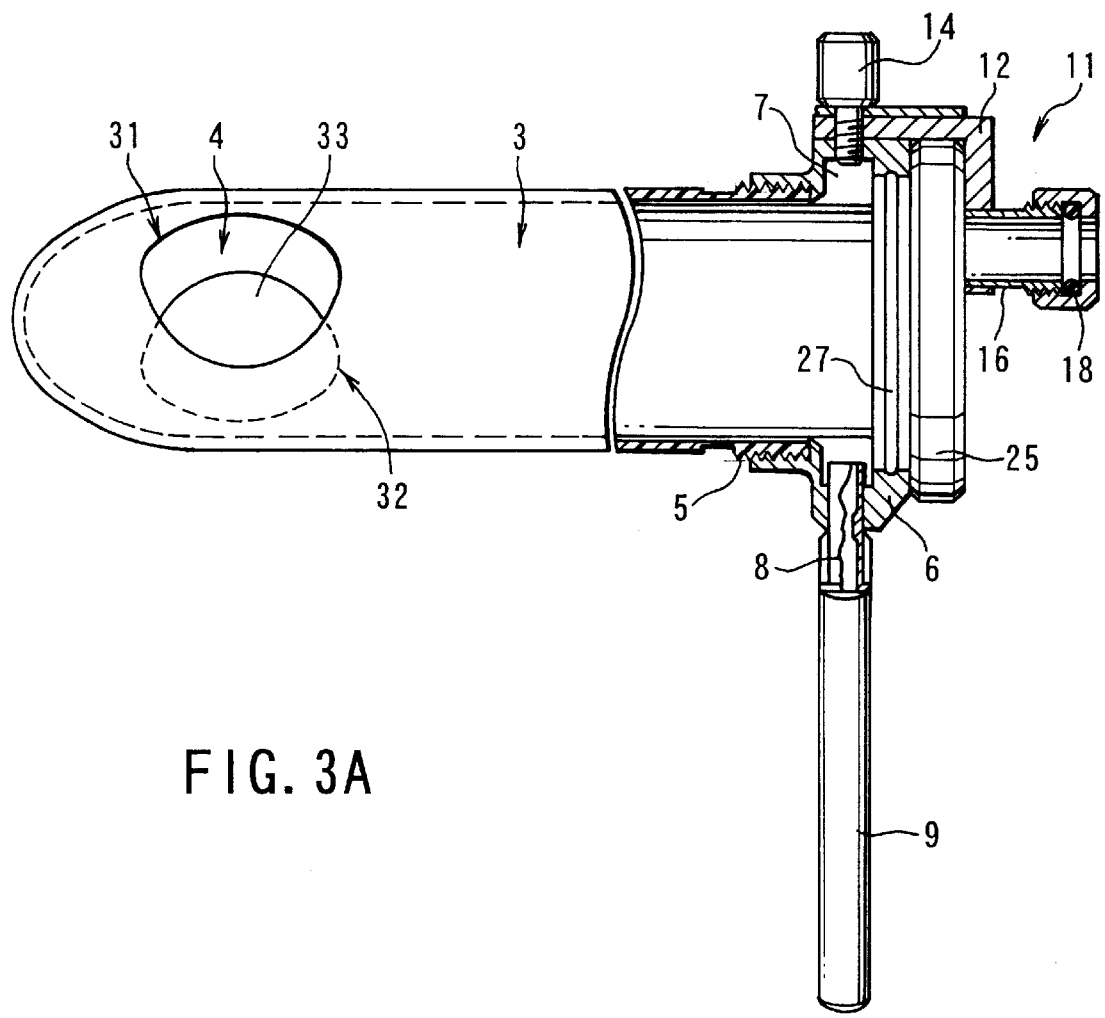
FIGS. 3A and 3B are explanative views showing a relation of the inner and outer sheaths of the endoscope guide tube unit of the first embodiment.

As shown in FIG. 3, a first opening 31 is provided, as a through hole, in the side wall of a near-distal-end portion of the outer sheath 3. Here, the first opening 31 is so formed as a side hole as to have an elliptical configuration whose minor axis is toward the axis of the outer sheath 3. A second opening 32 is provided as a through hole in the side wall of a near-distal-end portion of the inner sheath 4 and so formed as a side hole as to have an elliptical configuration whose minor axis is toward the axial direction of the outer sheath 3. The first and second openings 31 and 32 are correspondingly equal in position and substantially equal in size to each other.

Figure 3B:
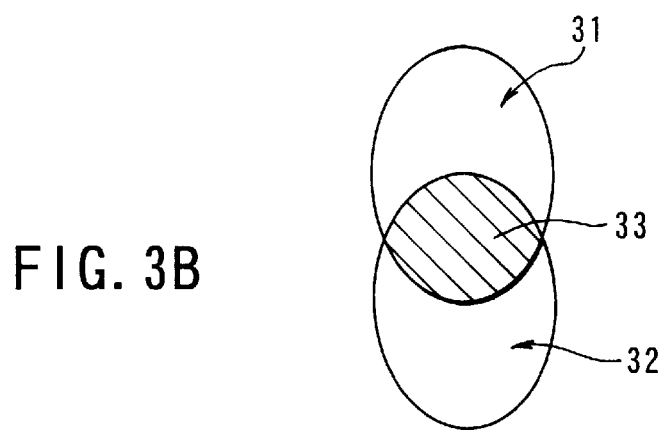

By rotating the second connector 25, it is possible to, as shown in FIG. 3, displace these openings 31, 32 in an not overlapped position, in a completely overlapped position or in a partly-overlapped position. By setting these openings at least in the partly-overlapped position, it is possible to define an opening as a whole of the device. By setting these openings 31 and 32 in the not-overlapped position, it is possible to close the opening as a whole of the device. FIG. 3B shows a development of the openings 31, 32. In FIG. 3B, a cross-hatched area corresponds to the overlapped area and an available treatment window 33 is defined by the overlapped area.

Figure 4:
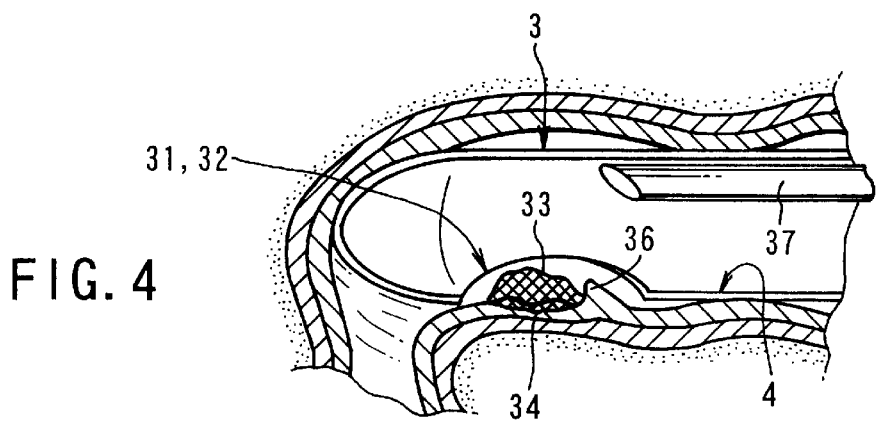
FIG. 4 is an explanative view showing a practical form of the endoscope guide tube unit of the first embodiment.

With reference to FIG. 4 an explanation will be given below about how to actually use the endoscope guide tube unit 1. With the inner sheath 4 fitted in the outer sheath 3 in a state as shown in FIG. 4, the endoscope guide tube unit 1 is assembled. Further, the first opening 31 of the outer sheath 3 and second opening 32 of the inner sheath 4 are displaced in the not-overlapped position where the treatment window 33 (that is, the openings 31, 32) is set in a closed state. In such a closed state, the insertion section 2 of the endoscope guide tube unit 1 is inserted into the rectus. At this time, since the treatment window 33 is closed, any rectal mucosa tissue portion is prevented from unduly entering into the endoscope guide tube unit 1 via the treatment window 33. This prevents any injury to the mucosa tissue. Further, the distal end of the outer sheath 3 has the streamlined curve, so that it is possible to prevent any injury to the tissue when the insertion section 2 is inserted into the body cavity. Further, since the distal-ends of the sheaths 3, 4 provide a streamlined curved surface, it is possible to prevent any diffused reflection of an observation beam and ensure a better observation when the body cavity is observed by the scope 37 beyond the distal-end of the sheaths 3, 4. It is also possible to check the body cavity for bleeding and compress any bleeding spot by the outer surface of the outer sheath to stop bleeding.

When the insertion section 2 is to be inserted into the rectal tract, it is done, while observing a scope image beyond the distal-end of the sheaths 3, 4, to a position where the first opening 31 corresponds to a lesion 34. At that position, the inner sheath 4 is rotated to open the treatment window 33 to a desired size. Even if the lesion 34 is situated at the backside of the rectal folds, this operation pushes the rectal folds by the outer surface of the outer sheath 3 to define a treatment plane. For this reason, it becomes possible to observe the lesion 34 and perform a treatment at all times under a stable condition.

Figure 5A:
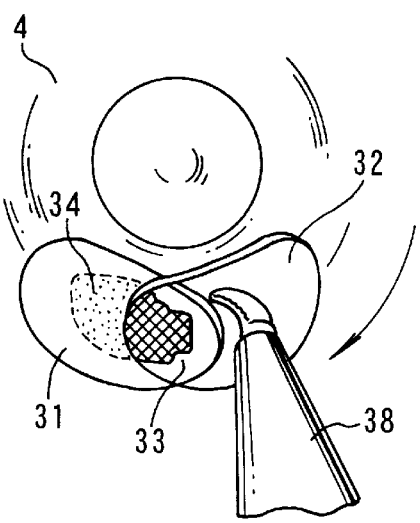
FIGS. 5A and 5B, each, are an explanative view showing a treatment performed on an endoscope guide tube unit of the first embodiment.
Figure 5B:
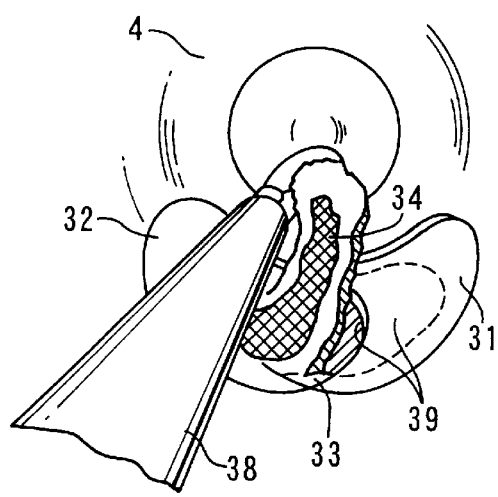

FIG. 5 shows a state in which any treatment is performed. As set out above, since the rectal mucosa is distended, the tissue portion readily enters via the opened treatment window 33 into the sheaths 3, 4. As a result, there is a risk that the treatment space will be narrowed. In order to prevent such a situation, the opened treatment window 33 is located only to a treating site as shown in FIG. 5A and the cutting-off of the lesion 34 by a treatment tool 38, such as forceps and surgical knife is progressed. And in accordance with this operation, the inner sheath 3 is rotated in a direction as indicated by an arrow in FIG. 5A and the opening position and size of the treatment window 33 are properly varied as shown in FIG. 5B.

In the case where the lesion 34 is cut off with the use of a high-frequency current, the field of vision is disturbed by smoke produced by the treatment done. In this case, a suction line is connected to the Luer-lock type connector 8 and a suction is effected through a clearance between the inner and outer sheaths to remove such smoke. For this reason, it is possible to perform a treatment under a better operation field. In addition, use is made, as the insertion section, of the transparent sheaths 3, 4 and, hence, a check is made to see whether or not there occurs any bleeding. It is also possible to compress the distal-ends of the sheaths against a bleeding cut-off wound to stop the bleeding. Needless to say, if use is made of an outer sheath 3 having a somewhat small opening 31, it is possible to avoid the narrowing of a treatment space by the mucosa and hence to perform a treatment by the outer sheath 3 only.

Figure 2C:
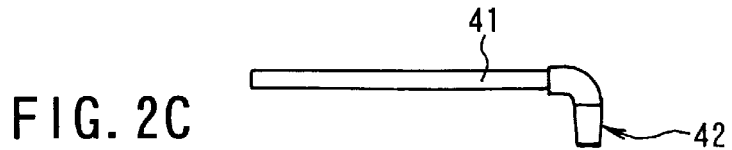
FIG. 2C is an explanative view showing a suction tube.

In the case where the treatment is performed by the outer sheath 3 only, a suction tube 41 as shown in FIG. 2C is connected to the Luer-lock type connector 8 as indicated by a broken line in FIG. 2A to provide a suction means for sucking smoke produced at the lesion as set out above. In the suction means, the portion of a taper section 42 bent toward the proximal-end portion of the suction tube 41 is fitted in a taper section of the inner surface of Luer-lock type connector 8 and, by doing so, it is possible to readily mount the suction tube 41 in the Luer-lock type connector 8.

After the cutting-off of the lesion 34, the parts of the cut-off wound are sewed together and, since the opening of the second connector 25 of the inner sheath 4 is enough great, it is possible to, while holding a sewing needle by a needle-carrier in an easy-to-use direction outside the body of a patient, guide the needle into the sheath 4. This operation is performed in a stitch-by-stitch fashion outside the body of the patient, so that it is not necessary to use any special technique such as a conventional continuous suture. In this case, since the inner cavity of the rectus is pushed by the outer peripheral surface of the outer sheath 3, there is no fear that there occurs a post-operation narrowing.

Figure 6:
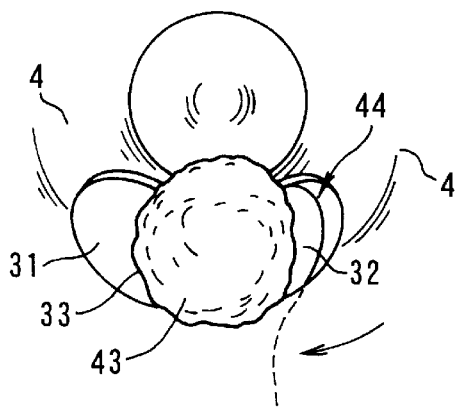
FIG. 6 is an explanatory view showing another treating (cutting-off) method by the endoscope guide tube unit of the first embodiment.

An explanation will be given below about an example of another cutting-off method. First, as in the case of FIG. 5, a treatment window 33 is created and, through the treatment window, an adequate physiological salt solution is fed at a site of the mucosa tissue portion to be cut off as shown in FIG. 6 and a region 43 to be cut off is expanded. Relative to the cut-off region 43, a high-frequency conduction wire 44 set about right-side one-half way around the opening 32 of the inner sheath 4, the inner sheath together with the wire 44 is rotated from the right-side while conducting the wire. By doing so, the cut-off region can be removed one at a time while stopping bleeding.

Figure 7:
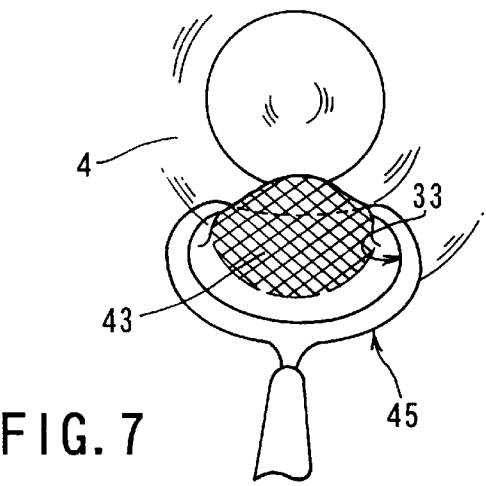
FIG. 7 is an explanative view showing still another treating (cutting-off) method by the endoscope guide tube unit of the first embodiment.

Still another cutting-off method will be explained below with reference to FIG. 7. In this case, a high-frequency snare 45 is set so as to surround the treatment window 33 between the outer sheath 3 and the inner sheath 4. As in the case of the example in FIG. 6, an adequate physiological salt solution is fed to a to-be-cut-off region of a mucosa tissue. After the region of the mucosa tissue is raised, the region is firmly clamped by a high-frequency snare 45 and the region is cut off by turning on the high-frequency snare 45. This method can more readily cut off the region than the previous method.

In the case where, in a surgery under a laparoscope, a treatment is performed on a deeply-seated narrow site in a treatment tract, etc., the present unit is inserted through the skin into the abdomen and set the treatment opening at a target tissue and, by doing so, it is possible to perform a ready treatment on the tissue under a better operation field.

Further the present unit can be applied to other cases, such as a treatment done through the vagina and at a tractless site such as a retroperitoneal space, etc.

Second Embodiment

An indoscope guide tube unit according to a second embodiment of the present invention will be explained below with reference to FIGS. 8A and 8B. This embodiment constitutes a variant of the first embodiment. Below an explanation will be given mainly about parts or elements differing from those of the first embodiment.

A cylindrical connection member 51 is threaded over the outer periphery of a proximal-side end of an outer sheath 3 and a first connector 6 is mounted on the connection member 51. A grip arm 9 is fixed to connection member 51 so as to support a whole apparatus. A fixing screw 52 is fixed to the first connector 6 and, by the fixed screw 52, the connection member 51 is clamped to the first connector 6. The connection member 51 is of such a type as to have a full-circle groove 53 around the outer periphery of the connection member 51. A forward end of the fixing screw 52 fixed to the first connector 6 is fitted in the engaging groove 53 and can clamp/fix the first connector 6 in place. That is, the first connector 6 is rotatable relative to the connection member 51 and can also be clamped/fixed by the fixing screw 52 to any given position.

A scope fixing tool 11 is selectively fixed to any of a plurality of recesses 54 in an inner wall of the first connector 6 of the outer sheath 3. The scope fixing tool 11 together with the connection member 51 is rotatable and, even if being located in a position eccentric from the center axis of the outer sheath 3, has its rotation position varied, so that it is possible to observe the whole surface of the outer sheath 3 even if, for example, an oblique-vision scope is used. In this case, use is made of a scope 37 for allowing a vision to be obtained in an oblique-vision direction of 30° or more. According to this, since the connector member is rotated, a whole surface of the sheath can be obtained in a field of vision even if the oblique-vision scope is used.

It is to be noted that the outer sheath may be used together with an inner sheath in a manner to have the inner sheath fitted in the outer sheath 3. The outer sheath may be used without using the inner sheath 4.

Third Embodiment

An endoscope guide tube unit according to a third embodiment of the present invention will be explained below with reference to FIG. 9. This constitutes a variant of the first embodiment of the present invention. Below, an explanation will be given principally about parts or elements differing from those of the first embodiment.

The distal-end of an outer sheath 3 is opened and an inner sheath 4 allows its distal-end to be extended or retracted through the distal-end opening 55. As in the case of the first embodiment, the inner sheath 4 has its distal-end closed. At a side wall of a near-distal-end portion of the inner sheath 4 an elliptical opening 32 is provided with its major axis set in an axial direction of the inner sheath 4. By enabling the distal-end portion of the inner sheath 4 to be projected from the distal-end opening 55 of the outer sheath 3, a projecting amount is adjusted, so that the size of a treatment window 33 is adjustable by defining the opening 32 in the side wall of the inner sheath 4.

Fourth Embodiment

An endoscope guide tube unit according to a fourth embodiment of the present invention will be explained below with reference to FIG. 10. This constitutes a variant of the first embodiment set out above. The variant will be explained, below, mainly about parts or elements differing from those of the first embodiment.

In this variant, an outer sheath 3 has an opening 61 defining a distal-end having an oblique edge and the distal-end of an inner sheath 4 is closed as in the first embodiment. In a near-distal-end side wall of the inner sheath 4 an elliptical opening 32 is provided with its major axis set in an axial direction of the inner sheath 4. By rotating the inner sheath 4, the opening 32 in the inner sheath 4 is opened and closed by the oblique end edge portion of the distal-end portion of the outer sheath 3. It is, therefore, possible to freely adjust the size of the opening above.

Fifth Embodiment

An endoscope guide tube unit according to a fifth embodiment of the present invention will be explained below with reference to FIGS. 11 to 13. This embodiment constitutes a variant of the first embodiment of the present invention. An explanation will be given, below, principally about parts or elements corresponding to those shown in conjunction with the first embodiment.

Figure 11A:
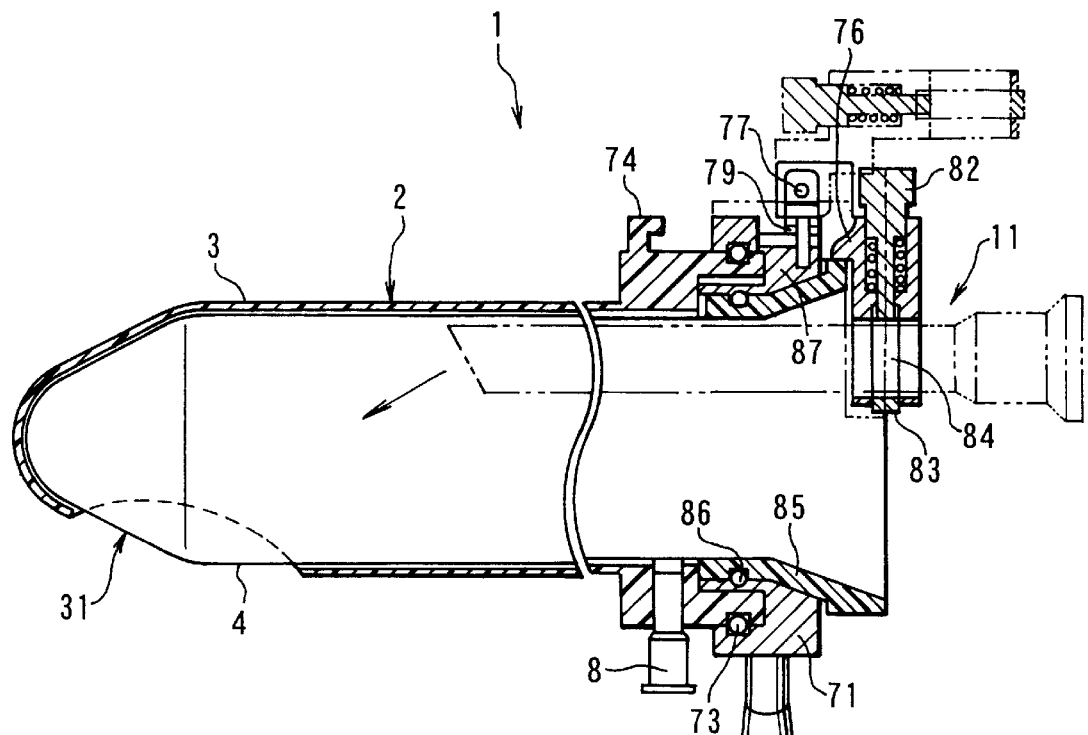
FIG. 11A is a view in longitudinal cross-section showing an endoscope guide tube unit according to a fifth embodiment of the present invention.
Figure 11B:
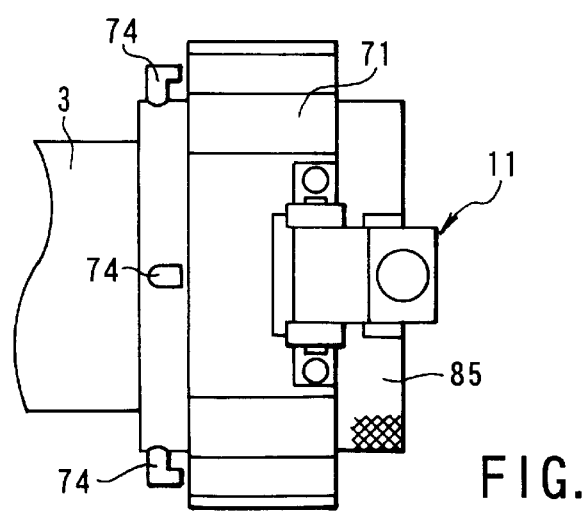
FIG. 11B is a plan view showing a proximal-end side area of the endoscope guide tube unit in FIG. 11A.
Figure 12:
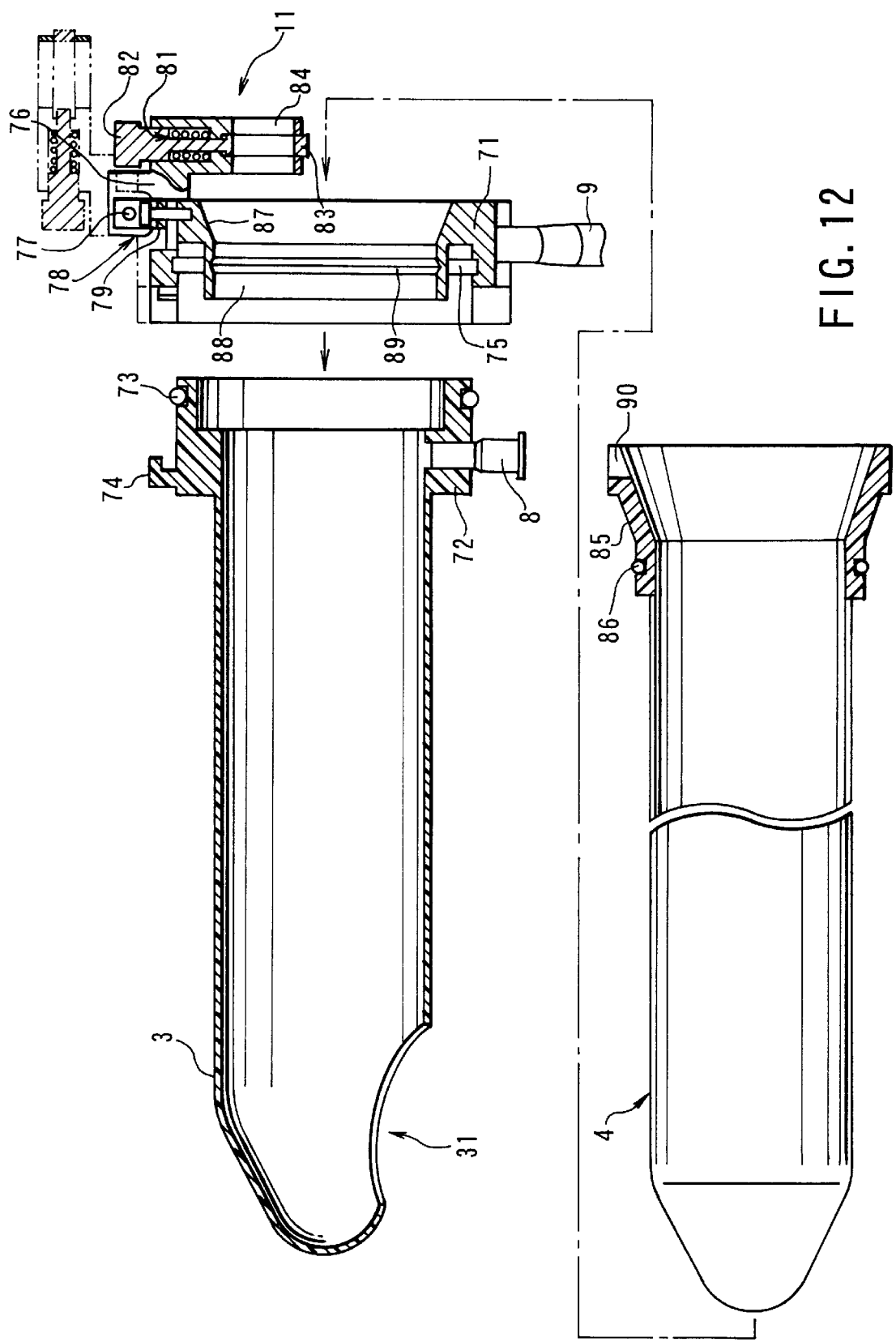
FIG. 12 is a view in longitudinal cross-section showing sub-assemblies in the endoscope guide tube unit according to the fifth embodiment.

FIG. 11A is an explanatory view showing a whole structure, in an assembled state, of an endoscope guide tube unit 1 of this embodiment. The endoscope guide tube unit 1 can be broadly classified into the three sub-assemblies an outer sheath 3, inner sheath 4 and connector 71.

First, the sub-assembly of the outer sheath 3 is of such a type as to have a streamlined distal-end portion and an opening 31 defined near the distal-end, the streamlined distal end portion being partly lacking due to the opening 31 merging therewith. A Luer-lock connector 8 is mounted at a proximal-end portion 72 of the outer sheath 3. An O-ring 73 and thread fixing sections 74 are provided at the outer periphery of the proximal-end portion 72.

A scope fixing tool 11 and fixing tool gripping arm 9 are mounted on the connector 71. In the inner wall of the forward end of the connector 71, a full-circle engaging groove 75 is provided. The portion of the proximal-end 72 of the outer sheath 3 is fitted into the inner wall portion of the forward end of the connector 71. When the connector 71 is fitted over the proximal-end 72 of the outer sheath 3, the O-ring 73 is intimately fitted in the groove 75, so that their engagement is insured.

The scope fixing tool 11 is retained at the forward end of an S-shaped support arm 76. The base end of the support arm 76 is pivotally attached to the connector 71 by a pin 77 provided at the member of the connector 71. When the inner sheath 4 is inserted into the outer sheath 3, the support arm 76 is swung about the pin 77 to bring the scope fixing tool 11 up to a one-side position indicated by a broken line in FIG. 11A.

At the support arm 78 of the scope fixing tool 11, a can 78 is formed around the pin 77 and a leaf spring 79 provided on the connector 71 is normally abutted against, and engages, the cam 78. When the support arm 76 is swung, the cam 78 depresses the leaf spring 79 down to produce a "click" sensation and the support arm 76 is held between an "in-use" position indicated by the solid line in FIG. 12 and the "one-side" position as indicated by a dot-dash line in FIG. 12.

A fixing means of the scope of the scope fixing tool 11 has a coil spring 81 provided inside the support arm 76, a push button 82 urged by a coil spring 81 and a fixing ring 83 connected to a forward end of the push button 82. The fixing ring 83 is so formed as to have an inner diameter equal to that of a scope retaining hole 84 in the support arm 76 and, upon depression of the push button 82, is located in a position coaxial with the scope retaining hole 84. The fixing ring 83 is normally so urged as to move upwardly under the coil spring 81. By depressing the push button 82 to allow the scope retaining hole 84 and fixing ring 83 to align with each other, the scope is inserted into both of the holes. Upon the release of the push button 82, the scope 81 is held by the fixing ring 83 trying to move upward under the action of the spring 81 and is fixedly fitted in the scope retaining hole 84.

Further, to the streamlined shape of the distal-end of the outer sheath 3 the counterpart of the inner sheath 4 is made equal, so that their distal-ends are intimately contacted with each other. In this variant, the inner sheath 4 does not possess an opening. The proximal-end portion 85 of the inner sheath 4 is outwardly flared and an elastic O-ring 86 is provided at the outer periphery of the proximal-end portion 85.

A mounting hole 88 is provided at the connector 71 and has a tapered mating section 87 corresponding to the proximal-end portion 85 of the inner sheath 71. In the inner wall surface of the mounting hole 88 a full-circumference groove 89 is provided and, when the inner sheath 4 is fitted in the outer sheath 3, the elastic O-ring 86 is fitted in the groove 89.

A groove-like holding section 90 adapted to engage with the support arm 76 is provided at the proximal-end 85 of the inner sheath 4. When the inner sheath 4 is fitted in the outer sheath 3, the support arm 76 provided at the connector 71 is set in a position indicated by a solid line in FIG. 12. By doing so, the portion of the support arm 76 is abuttingly fitted in the holding section 90 to hold the inner sheath 4 in the outer sheath 3.

When the above-mentioned sub-assemblies are combined together, the connector 71 is fitted over the outer sheath 3 and, after bringing the scope fixing tool 11 to an upper one-side position, the inner sheath 4 is inserted via the connector 71 into, and fitted in, the outer sheath 3. In this state, the outer sheath 3 and inner sheath 4 are sealed by the O-rings 73, 86 therebetween except at the opening 31. When, therefore, the sheaths 3, 4 are inserted into the rectal tract, it is possible to expand the intestinal tract, by supplying a gas from the Luer-lock connector 8, and to effect a safer insertion operation. In this connection it is to be noted that, with the inner sheath 4 drawn off, a treatment can be performed using the opening of the outer sheath 3 as a treatment window 33.

An explanation will be given below about how to use the endoscope guide tube unit 1. In general, the operability of the treating tool such as the forceps depends greatly upon the length and inner diameter of the sheath. The longer the sheath, and the smaller the inner diameter of the sheath, the worse the operability.

One solution is by, as in the first embodiment, changing the length of the sheath to a proper one depending upon the depth of a lesion situated. Here an explanation will be given below, while referring to FIG. 13, about how to draw the lesion toward the proximal-end side.

Using the assembled unit as shown in FIG. 11A, the sheaths are inserted into the rectal tract and, after the inner sheath 4 only is drawn off, threads 92 tie on the rectal tissue portion 91, by a needle carrier, etc., at the opening 31 through the outer sheath 3 and are guided to an outside via the opening of the connector 72. This operation is performed on the surrounding region of the rectal tract and this is done while rotating the outer sheath 3 and hence moving the opening 31. Then the outer sheath 3 is pulled out.

Then, while pulling the threads 92, the outer sheath 3 is again inserted in a manner to allow the threads to lie along the outer surface of the outer sheath 3. Through an observation under the scope, the threads 92 are pulled to a position where the lesion 93 is displaced to the opening 31. Once the position of the lesion 93 is determined, the thread 92 ties on the corresponding thread fixing section 74 to fix the lesion 93 in place. As already set out above, the rectal tissue portion 91 is developed in nature and, if being pulled toward the user side, it is possible to draw the lesion 93 considerably up to the proximal-end side.

Figure 13:
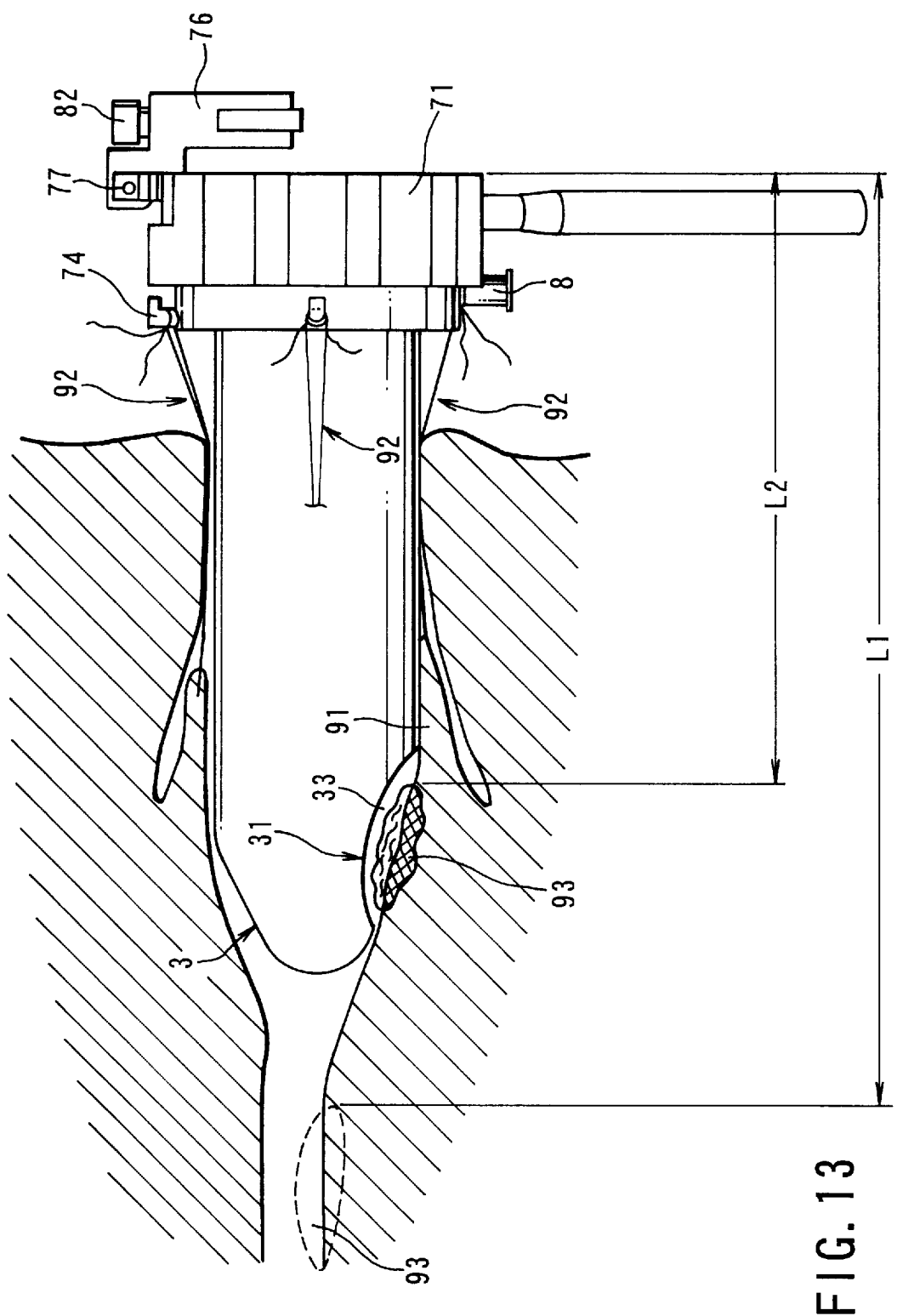
FIG. 13 is an explanative view showing an in-use state showing the endoscope guide tube unit of the fifth embodiment.

As shown in FIG. 13, the lesion 93 can be treated in a position L2 shallower than an initial deep position L1 and it is, therefore, much easier to treat it.

Sixth Embodiment

With reference to FIGS. 14 to 20, an explanation will be given below about an endoscope guide tube unit. This embodiment constitutes a variant of the first embodiment and will be explained, below, principally about parts and elements differing from those of the first embodiment.

Figures 14A, 14B:
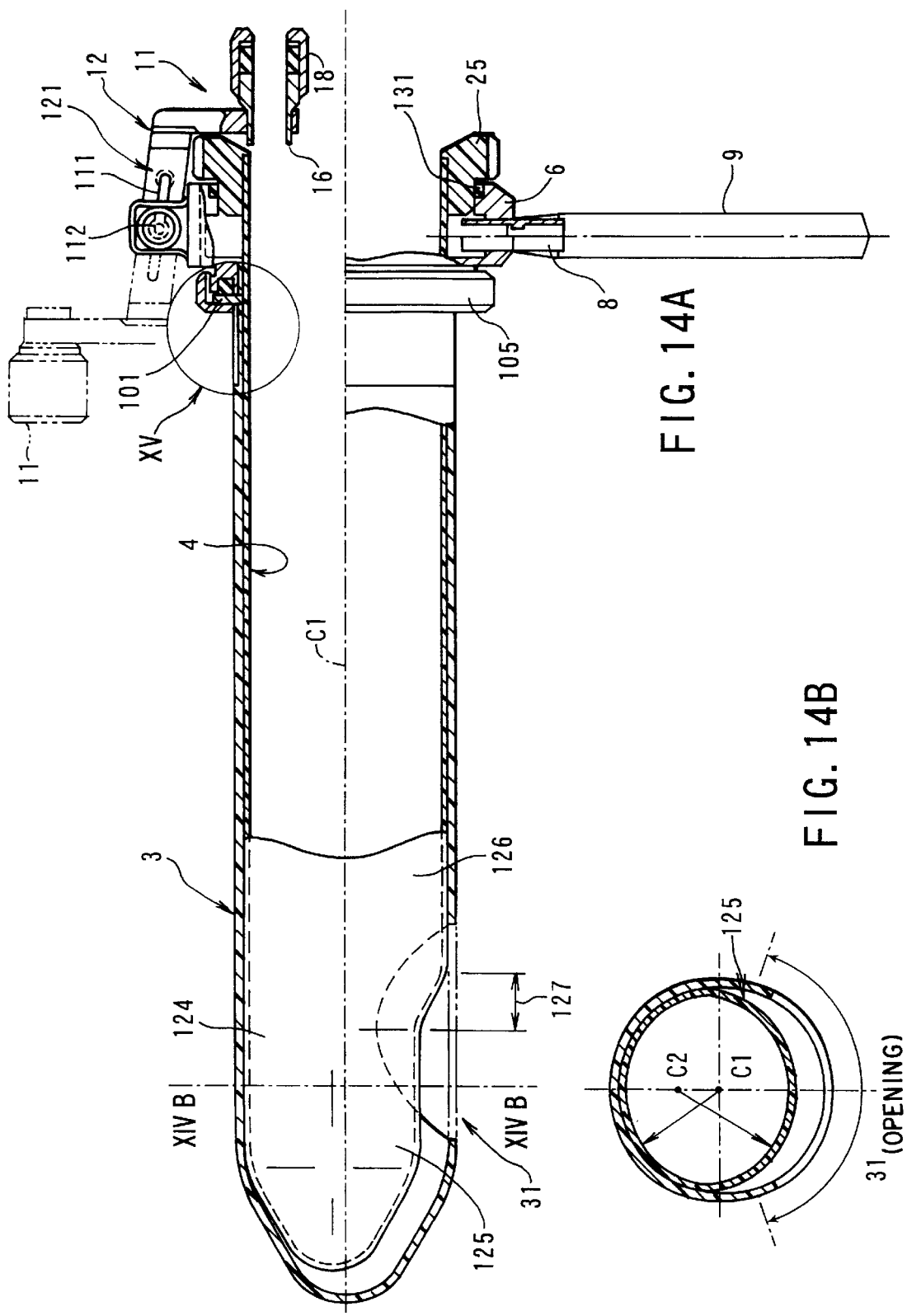
FIG. 14A is a view in longitudinal cross-section showing sub-assemblies of outer and inner sheaths of an endoscope guide tube unit according to a sixth embodiment of the present invention.
FIG. 14B is a view in transverse cross-section, as taken along line XIVB—XIVB in FIG. 14A.
Figure 15:
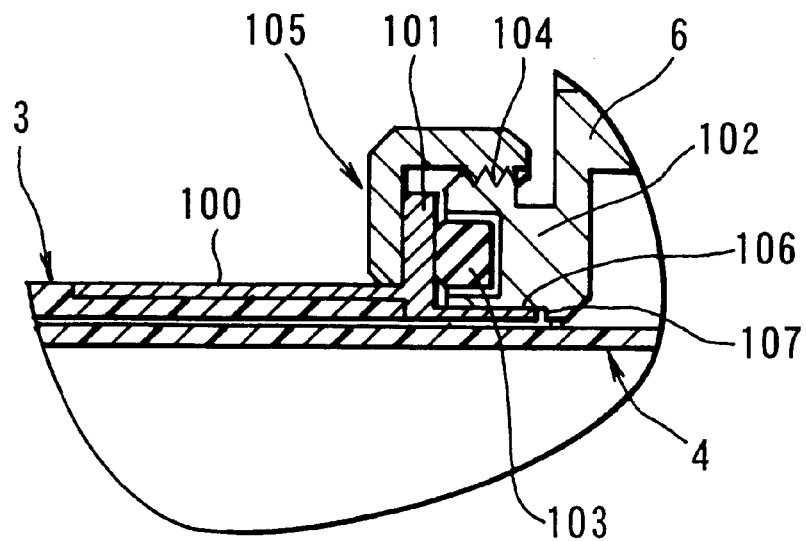
FIG. 15 is a view in longitudinal cross-section showing an XV area in FIG. 14A as an enlarged area.

As shown in FIGS. 14 and 15, a cylindrical flange member 100 is fixedly mounted, in a coaxial relation, on the distal-side end of an outer sheath 3 of the endoscope guide tube unit 1 and an outwardly extending flange 101 is provided on the flange member. 100. Further, a forward-end cylindrical section 102 is formed on the forward end of the first connector 6 in an opposed relation to the flange 101. A ring-like elastic member 103 is arranged on the forward end surface portion of the cylindrical section 102 so as to face the flange 101. A threaded section 104 is provided on the outer periphery of the forward-end cylindrical section 102. The flange 101 is secured to the first connector 6 by inserting a fastening member 105 over the threaded section 104. And the face of the flange 101 is pushed against the elastic ring 103 to secure a hermetic seal there.

At the proximal-side end portion of the outer sheath 3 the rear end portion of the flange member 100 provides a cylindrical projection 106 somewhat extending from the face of the flange 101 toward the user's side. By inserting the projection 106 into a groove 107 in the inner wall surface of the forward-end cylindrical section 102 of the first connector 6 the center axis of the first connector 6 is set in alignment with that of the outer sheath 3.

A scope fixing tool 11 is held in place by one end portion of an L-shaped arm 12 extending from the first connector 6 as set out above. A slit-like cam hole 111 is provided in the other end portion of the arm 12 in a manner to define a given angle relative to the center axes of the inner and outer sheaths 4 and 3 in the in-use state of the scope. The arm 12 is mounted in place by inserting a pin 112 on the first connector 6 side into the cam hole 111.

The scope fixing tool 11 can be swung about the pin 112 from a position as indicated by a solid line to a position as indicated by a dot-dash line in FIG. 14A. Further, in the state as shown in the dot-dash line, the inner sheath 4 can be removed from the outer sheath 4. The scope fixing tool 11 is slidable in a direction of the cam hole 111 in which the pin 112 is inserted and, if so sliding toward the forward-end side, the scope fixing tool 11 allows its whole structure to be moved somewhat upwardly. By doing so, it is possible to prevent any clearance from being created between the inner surface of the outer sheath 3 and the scope.

Figure 16:
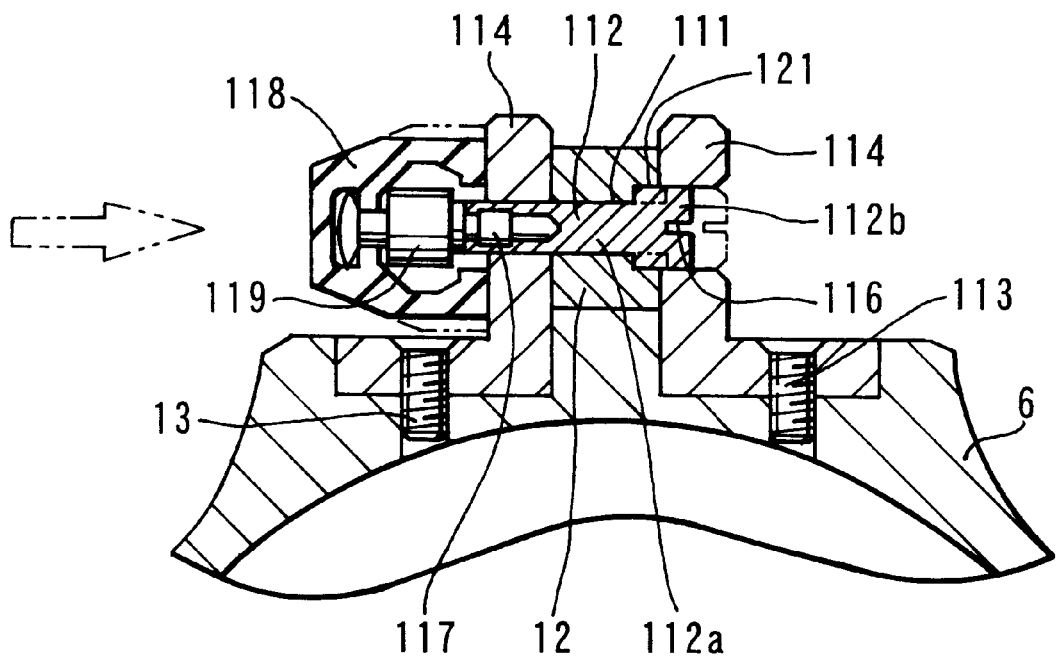
FIG. 16 is a view in transverse cross-section showing a pin and its surrounding area as an enlarged area.

As shown in FIG. 16, the pin 112 is so fitted as to extend through a pair of support plates 114 which are fixed by a screw means to the first connector 6. The pin 112 has a head 112b, at one end, having a diameter greater than that of a shank 112a of the pin. A recess 16 is provided at the head 115 to allow a driver, not shown, which rotates the shank 112a to engage therewith. The shank 112a has an internally threaded section 117 at its other end portion and a core member 119 for holding an elastic member 118 is threaded into a internally threaded section. The elastic member 118 is comprised of a cap-like member made of an elastic material, such as a rubber. The elastic member 118 is so located as to be opposite to the outer wall of one of the support plates 114.

A counterbore 121 is formed at each end of the cam hole 111. The head (step) 112b of the arm 12 fitted in the cam hole 111 is seated in the counterbore. 121 and, at this time, the sliding of the pin 112 is prevented. When the arm 12 is pushed by pushing the elastic member 118, the head 112b of the pin 112 which is seated in the counterbore 121 is moved away from the counterbore 121 to release the pin 112. As a result, the pin is slidable along the cam hole 111.

Figure 17:
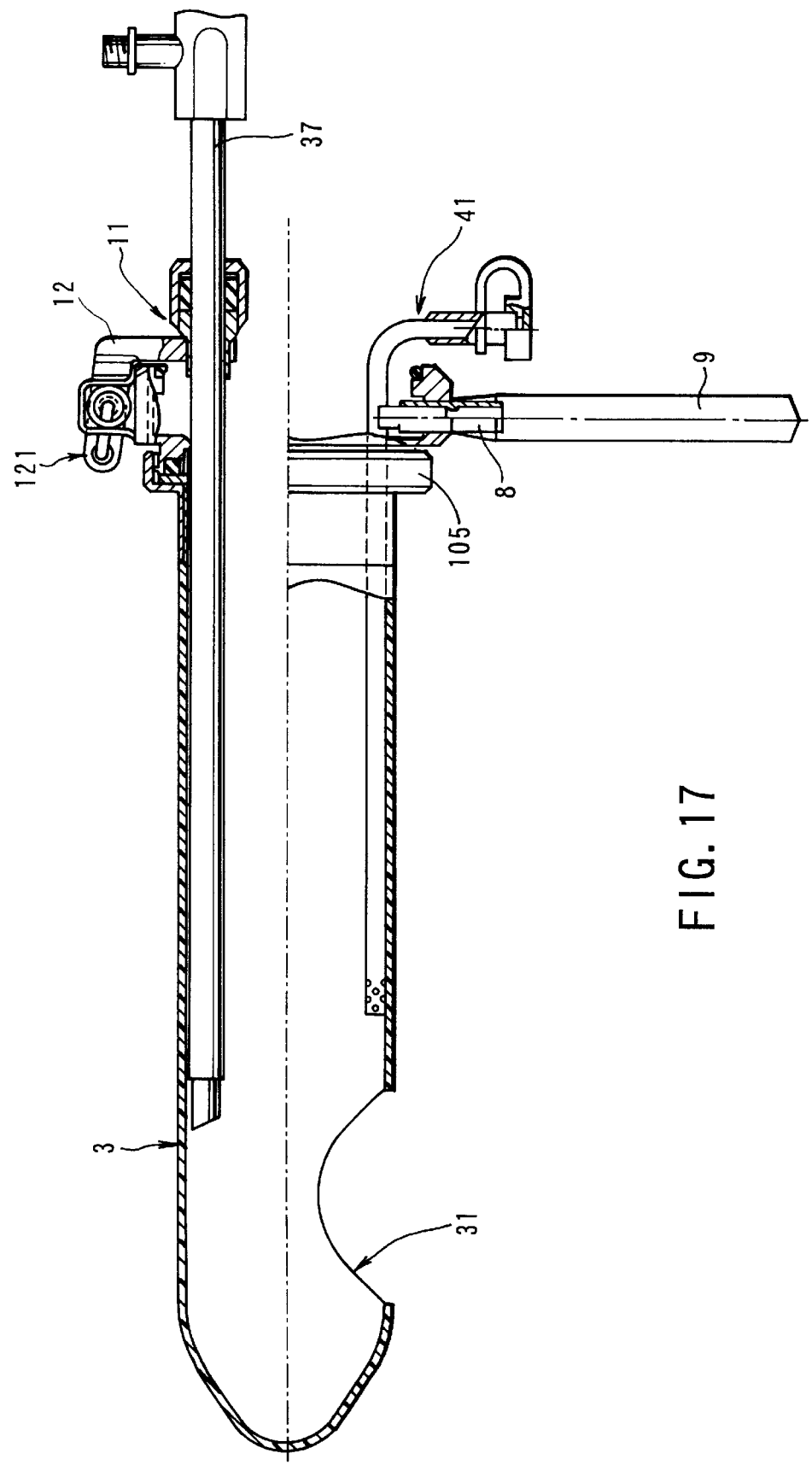
FIG. 17 is a view in longitudinal cross-section showing a sub-assembly of an outer sheath in an endoscope guide tube unit according to a sixth embodiment of the present invention.

FIG. 17 shows a state in which a treatment is performed. As set out above, the inner sheath 4 is removed from the outer sheath 3 and, by moving the arm 12 in slide motion, the scope fixing tool 11 is located on the forward-end side and the scope is mounted on the scope fixing tool 11. A suction tube 41 is positioned in the inner sheath 4 and is set. In this state, a lesion 34 positioned at an opening 31 of the outer sheath 3 is treated, while observing the scope image.

Figure 18A:
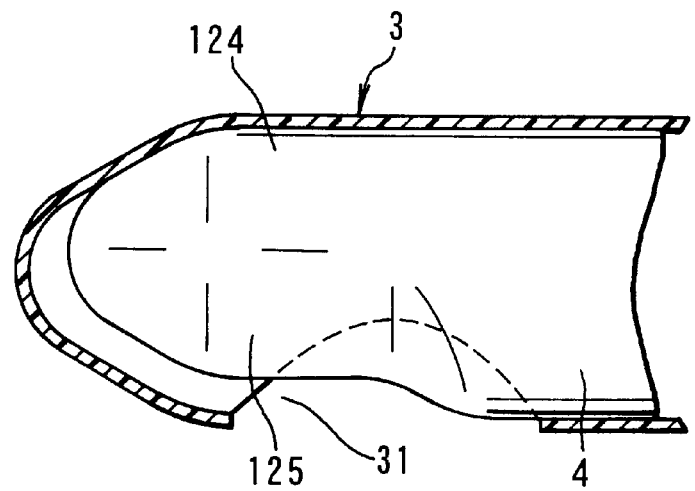
FIGS. 18A and 18B are views in longitudinal cross-section showing a configuration relation of a distal-end portion of the outer sheath and that of the inner sheath arranged in the outer sheath in the endoscope guide tube unit of the sixth embodiment.
Figure 18B:
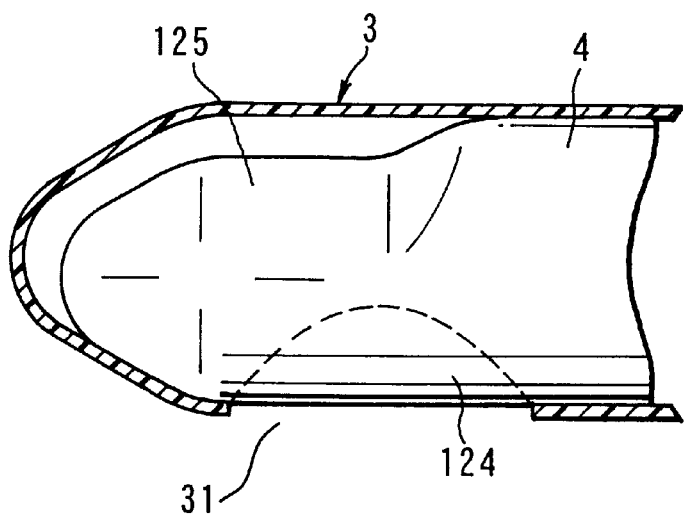
Figure 19:
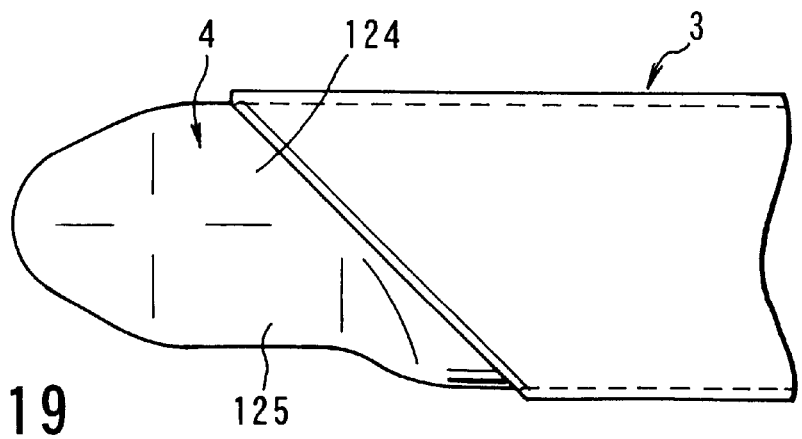
FIG. 19 is a side view showing another configuration relation showing the distal-end portion of the outer sheath and that of the inner sheath arranged in the outer sheath in the endoscope guide tube unit of the sixth embodiment.
Figure 21A:
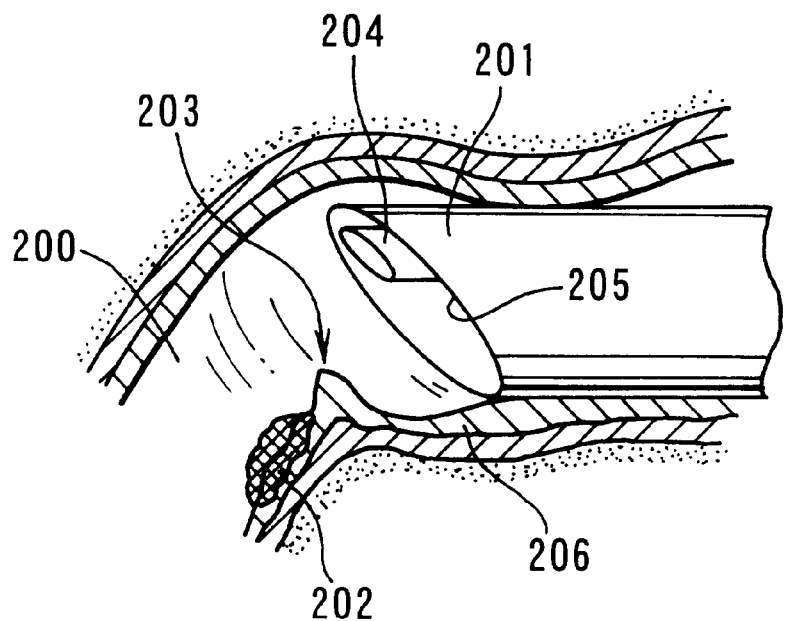
FIGS. 21A and 21B, each, show an in-use state of a conventional endoscope guide tube unit.
Figure 21B:
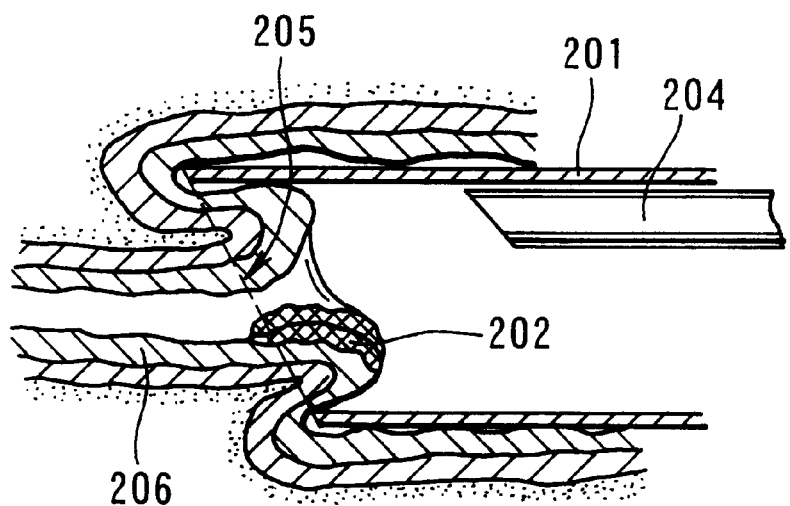

Now an explanation is given below about the configuration of the distal-end of the inner sheath 4. As shown in FIGS. 14A, 14B, 18A and 18B, the distal-end of the inner sheath 4 is closed and differs in configuration from the outer sheath 3. That is, as shown in FIG. 14B, the configuration of the distal-end of the inner sheath 4 comprises a surface 124 whose center coincides with a center (C1) of the outer sheath 3, a surface 125 (center C2) offset from a center (C1) of the outer sheath 3, and a shift range 127 smoothly joining the offset surface 125 to a proximal-end-side outer surface 126. It is to be noted that the maximal end portion 128 of the inner sheath 4 defines a somewhat small-diameter round-headed conical configuration relative to the outer sheath 3. The shift range 127 is positioned more toward the proximal-end side than generally at a center of the first opening 31. By defining the distal-end portion of the inner sheath 4 as set out above, the inner sheath 4 can be selectively rotated, relative to the outer sheath 3, to a first position where the first opening 31 is blocked and to a second position where the first opening 31 is opened. This configuration can be applied to an outer sheath 3 whose distal-end is obliquely opened as shown in FIG. 19. In this case, the sheaths 3, 4 may be determined so as to push a lesion 34 against an offset surface side.

The inner sheath 4 having such a configuration at the distal end has an advantage in that it is possible to prevent a mucosa from being injured at the opening 31 when the sheaths are inserted into, and withdrawn from, the rectal tract. In the case where the sheaths are actually inserted into the rectal tract, an air feeding pump, for example, what is called a "double bulb" is mounted at the Luer-lock connector B. By doing so, air is fed into the rectal tract via the opening 31 and, while expanding the rectal tract with the air, the endoscope guide tube unit 1 is inserted. Here, the inner surface of the first connector 6 of the outer sheath 3 is coupled by a sealing member 131 to a second connector 25 of the inner sheath 4. When the endoscope 1 is inserted, the first opening 31 of the outer sheath 3 is closed by the distal-end portion of the inner sheath 4 as shown in FIG. 18B.

On the other hand, when the endoscope guide tube unit 1 is removed away from the rectum after a treatment is effected, an inner sheath 4 is inserted into the outer sheath 3 in a way to have the offset surface 125 of the inner sheath 4 substantially correspond to the opening 31 of the outer sheath 3. If the inner sheath 4 is inserted into the outer sheath 3 in that orientation, it is possible to avoid the situation in which a mucosa tissue intruded into the interior of the outer sheath 3 from the first opening 31 is injured by being trapped between the surrounding area of the first opening 31 and the inner sheath 4.

Thereafter, the air is fed by the double bulb in the same way as at the insertion time and the inner sheath 4 is rotated while allowing the tissue which is situated near the opening 31 of the outer sheath 31 to be pushed out of the opening 31. And the opening 31 of the outer sheath 31 is closed by the distal end portion of the inner sheath 4. At this time, the first opening 31 is closed while pushing the tissue out of the first opening 31 by supplying the air there. Therefore, there is no risk that the mucosa tissue will be injured by the opening 31. After the first connector 31 is closed by the inner sheath 4, the sheath may be withdrawn directly from the rectal tract. It is to be noted that these operations are done all under the observation of the scope.

An explanation will be given below about the technique of removing only a mucosa tissue in a human body with the use of the guide tube unit 1 of the present invention. It is the usual practice to, relative to a lesion staying in the mucosa tissue, inject a physiological salt solution at the surrounding region of the lesion and remove the mucosa tissue in a flatted (or separated) state.

Here, an explanation will be given about the treating method combining a laser surgical knife as a means of cutting off the mucosa tissue and a laser beam absorbing material, such as a solution called an ICG (endocyanine green) solution. It is to be noted that, as the laser surgical knife, use is made of a semiconductor laser having a waveform of 805 nm. Further, the ICG solution has the feature that it has an absorption spectrum in a living body substantially equal to the wavelength of the semiconductor laser and that it more effectively absorbs laser light than an ICG-free living tissue portion.

Hereinbelow, an explanation will be given about how to cut off the mucosa tissue portion.

(1) First, as shown in FIG. 20A, checking is made to see, through the microscope observation at the opening 31, a lesion staying in the muscosa tissue.

(2) Then, as shown in FIG. 20B, a local injection needle 141 combined with an applicator 141 is acquired in a visual field of the endoscope.

(3) With the tip portion of the local injection needle 141 extended in the visual field of the endscope, the needle tip penetrates the surrounding region of the lesion 34 and, further, a layer what is called a mucosa underlayer 142 of the muscosa tissue and injects the ICG solution. Thereafter, checking is made to see whether or not the lesion 34 is adequately raised (see FIGS. D to E). At this time, the ICG solution 143 is present below the mucosa tissue and the mucosa tissue is in a state separated at an adequate distance from a muscle layer 144 below the mucosa underlayer 142.

(4) Then the local injection needle 141 is removed from the applicator 140 and, instead, a laser probe 145 of a surgical laser knife is mounted on the applicator 140. As shown in FIG. 20E, the tip portion of the laser probe 145 is contacted with the surrounding region of the lesion 34 and starts cutting off the lesion. At this time, the ICG below the mucosa absorbs a laser beam and, therefore, the laser beam is less likely to be transmitted to the muscle layer deeper than the mucosa underlayer 142 where the ICG is present.

(5) By doing so, the mucosa underlayer 142 is positively cut off as shown in FIG. 20F, without injuring the muscle layer, and a lesion staying in the mucosa tissue can be cut off one at a time.

The method of the present invention is applied to the procedure of cutting off a gastrointestinal (including a rectum) tract region in particular, characterized in that no bleeding occurs at the mucosa tissue along the mucosa underlayer and the lesion can be positively cut off while suppressing a thermal injury to a lower extent. Fur this reason, there is the greatest advantage in that, in comparison with the conventional cutting-off technique using an electric surgical knife, the situations of causing an injury to the muscle layer or a penetration hole are avoidable.

Although, in the above-mentioned embodiment, the semiconductor laser is used in combination with the ICG solution, the same advantage can be obtained so long as the wavelength of the laser is substantially equal to the absorption spectrum of a solution combined therewith.

Additional advantages and modifications will readily occurs to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope guide tube unit comprising:
   a first elongated sheath-like member adapted to be inserted into a body cavity of a subject, said first sheath-like member having a side wall section and a closed distal-end section and having a mouth section at a proximal end through which an endoscope and at least one treatment tool are insertable, wherein the side wall section has an opening through which the affected region is treated, and wherein the mouth section is dimensioned such that both the endoscope and the at least one treatment tool can be freely inserted at the same time and such that the at least one treatment tool can be operated to be freely moved within the first sheath-like member to treat the affected region;
   a holder provided on a proximal-end side of the first sheath-like member to hold the endoscope in place; and
   a second sheath-like member telescopically inserted into the first sheath-like member and having a section for closing the opening through which the affected region is treated.

2. An endoscope guide tube unit according to claim 1, wherein the mouth section is formed of a member separate from the first sheath-like member and has a wide mouth substantially equal in size to an inner size of the first sheath-like member.

3. An endoscope guide tube unit according to claim 1, wherein the mouth section is formed of a member separate from the first sheath-like member and the separate member is removable from the first sheath-like member.

4. An endoscope guide tube unit according to claim 1, wherein the mouth section is formed of a member separate from the first sheath-like member and the separate member is mounted on the first sheath-like member so as to be rotatable around the first sheath-like member.

5. An endoscope guide tube unit according to claim 1, wherein the holder holds an oblique-viewing scope in place.

6. An endoscope guide tube unit according to claim 1, wherein the first sheath-like member is transparent at least at an area from a distal end to a proximal-side end thereof.

7. An endoscope guide tube unit according to claim 1, wherein the first sheath-like member has a rounded distal-end.

8. An endoscope guide tube unit according to claim 1, wherein a distal-end portion of the first sheath-like member is elastically flexible.

9. An endoscope guide tube unit according to claim 1, wherein an outer surface of a distal-end of the first sheath-like member has a streamlined, curved surface.

10. An endoscope guide tube unit according to claim 1, wherein the second sheath-like member has an opening at a distal-end portion, and wherein the opening of the second sheath-like member and the opening of the first sheath-like member are adapted to overlap each other to provide a common area for a treatment window and are adapted to be displaced with respect to each other to close the treatment window.

11. An endoscope guide tube unit according to claim 10, wherein the first and second sheath-like members are transparent at least at an area from a distal end to a proximal-side end thereof.

12. An endoscope guide tube unit according to claim 1, further comprising a suction passage communicating from a proximal-end side of the first sheath-like member to the opening through which the affected region is treated to suck a gas present at the opening and at an area surrounding the opening through the suction passage.

13. An endoscope guide tube unit according to claim 12, wherein the suction passage is provided as a clearance between an inner surface of the first sheath-like member and an outer surface of the second sheath-like member and communicates with the opening through which the affected region is treated.

14. An endoscope guide tube unit according to claim 13, further comprising:
   a seal, located more on a proximal-end side than at the opening, for sealing the clearance; and
   a suction mouth section connected to the suction passage and communicating with a suction source.

15. An endoscope guide tube unit according to claim 1, wherein the opening has an elliptical configuration with a minor axis situated in an axial direction of the first sheath-like member.

16. An endoscope guide tube unit according to claim 1, further comprising a seal which hermetically seals a clearance defined between the first and second sheath-like members when the second sheath-like member is arranged in the first sheath-like member, wherein the second sheath member has a first section on an outer surface thereof adapted to close the opening through which the affected region is treated and a second section adapted to move away from the opening to define a clearance relative to the opening, and wherein the second sheath member is rotatable and movable along an axial direction relative to the first sheath-like member.

17. An endoscope guide tube unit according to claim 1, further comprising a cutting-off member arranged at least one-half way around the opening through which the affected region is treated.

18. An endoscope guide tube unit according to claim 1, further comprising a high-frequency snare wire arranged between the first sheath-like member and the second sheath-like member so as to surround a full-circumference of the opening through which the affected region is treated.

19. An endoscope guide tube unit according to claim 1, wherein the first and second sheath-like members are adapted to be rotatable relative to each other.

20. An endoscope guide tube unit according to claim 1, further comprising a connector member connected to the first sheath-like member to wholly support the first sheath-like member, and at least one thread fixing member provided on the connector member.

21. An endoscope guide tube unit according to claim 1, further comprising a grip section connected to the first sheath-like member to wholly support the first sheath-like member.

22. An endoscope guide tube unit according to claim 1, further comprising a grip section connected to the second sheath-like member to wholly support the second sheath-like member.

23. An endoscope guide tube unit according to claim 1, wherein an outer surface of a near-distal-end area of the second sheath-like member has a first outer peripheral surface with a same center axis as the first sheath-like member and a second outer peripheral surface as an offset surface having a parallel-shifted center axis.

24. An endoscope guide tube unit according to claim 23, wherein the first sheath-like member has a rounded distal-end.

25. An endoscope guide tube unit comprising:
   a first elongated sheath-like member adapted to be inserted into a body cavity of a subject, said first sheath-like member having a side wall section and a distal-end section and having a mouth section at a proximal-end side of the first sheath-like member through which at least one treatment tool and an endoscope is insertable, wherein the side wall section has a first opening through which the affected region is treated, and wherein the mouth section is dimensioned such that both the endoscope and the at least one treatment tool can be freely inserted at the same time and such that the at least one treatment tool can be operated to be freely moved within the first sheath-like member to treat the affected region;
   a holder provided on a proximal-end side of the first sheath-like member and adapted to hold an endoscope in place which, in use, is inserted via the mouth section into an inside of the first sheath-like member; and
   a second sheath-like member telescopically inserted into the first sheath-like member and having a closing portion for closing the first opening, and a second opening overlapped with the first opening,
   wherein the first and second sheath-like members are selectively relatively movable between a first position in which the first opening is closed by the closing portion of the second sheath-like member and a second position in which the first and second openings are overlapped to provide a common opening area defining a treatment window via which the affected region is treated.

26. An endoscope guide tube unit according to claim 25, wherein an outer surface of a near-distal-end area of the second sheath-like member has a first outer peripheral surface with a same center axis as the first sheath-like member and a second outer peripheral surface as an offset surface having a parallel-shifted center axis.

27. An endoscope guide tube unit according to claim 25, wherein the first and second sheath-like members are relatively rotatable with respect to each other.

28. An endoscope guide tube unit according to claim 25, wherein the first and second sheath-like members are relatively movable with respect to each other via a sliding motion in an axial direction.

29. An endoscope guide tube unit according to claim 25, wherein the first sheath-like member is closed at a distal-end thereof.

30. An endoscope guide tube unit according to claim 29, wherein an outer surface of the distal-end of the first sheath-like member is streamlined and closed.

31. An endoscope guide tube unit according to claim 25, wherein a distal-end of the second sheath-like member is opened.

32. An endoscope guide tube unit according to claim 25, wherein:
   the first sheath-like member is opened at a distal-end thereof;
   and an outer surface of a distal-end of the second sheath-like member is streamlined and a distal-end portion of the second sheath-like member is adapted to be projected via the opened distal-end of the first sheath-like member.

33. An endoscope guide tube unit according to claim 25, wherein the first and second openings are formed as elliptical openings each with a minor axis defined in an axial direction of the first sheath-like member.

34. An endoscope guide tube unit according to claim 25, further comprising a seal hermetically sealing a clearance defined between the first and second sheath-like members when the second sheath-like member is arranged inside of the first sheath-like member, wherein the second sheath-like member has a first portion on an outer surface thereof adapted to close the first opening and a second portion adapted to be shifted away from the first opening to define a clearance relative to the first opening, and wherein the second sheath-like member is rotatable and movable in an axial direction relative to the first sheath-like member.

35. An endoscope guide tube unit according to claim 25, further comprising a cutting-off member provided at least one half way around the treatment window.

36. An endoscope guide tube unit according to claim 25, further comprising a high-frequency snare wire between the first sheath-like member and the second sheath-like member so as to surround a full-circumference of the treatment window.

37. A method for cutting off a mucosa tissue in a rectal tract with an endoscope guide tube unit according to claim 20, comprising the steps of:
   inserting a needle carrier having threads attached thereto, into the endoscope guide tube unit via an associated connector, and anchoring the threads to the mucosa tissue through the opening in the side wall section of the first sheath-like member near a distal-end portion of the guide tube unit;

pulling the anchored threads from the connector to an outside past an interior of the endoscope guide tube unit;

drawing the guide tube unit out of the rectal tract to leave the anchored threads only;

again inserting the guide tube unit into the rectal tract, while pulling the anchored threads along an outer surface of the guide tube unit;

drawing the anchored threads further backward to a position in a vicinity of the opening where a target mucosa tissue portion can be treated via the opening;

fixing the threads to the thread fixing member; and cutting off the target mucosa tissue portion.

* * * * *